US009788819B2

(12) United States Patent
Householder et al.

(10) Patent No.: US 9,788,819 B2
(45) Date of Patent: Oct. 17, 2017

(54) INTRODUCER FOR BIOPSY DEVICE

(71) Applicant: Devicor Medical Products, Inc., Cincinnati, OH (US)

(72) Inventors: Robert M. Householder, Loveland, OH (US); Edward A. Rhad, Fairfield, OH (US); Andrew Paul Nock, Dayton, OH (US); Kevin M. Fiebig, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 48 days.

(21) Appl. No.: 14/700,406

(22) Filed: Apr. 30, 2015

(65) Prior Publication Data

US 2015/0313579 A1 Nov. 5, 2015

Related U.S. Application Data

(60) Provisional application No. 61/987,215, filed on May 1, 2014.

(51) Int. Cl.
*A61B 5/00* (2006.01)
*A61B 10/02* (2006.01)
(Continued)

(52) U.S. Cl.
CPC ...... *A61B 10/0283* (2013.01); *A61B 10/0233* (2013.01); *A61B 10/0275* (2013.01);
(Continued)

(58) Field of Classification Search
CPC . A61B 10/02; A61B 10/0233; A61B 10/0266; A61B 10/0275; A61B 10/0283;
(Continued)

(56) References Cited

U.S. PATENT DOCUMENTS 4,023,559 A * 5/1977 Gaskell ................. A61B 10/02
600/572
4,318,414 A * 3/1982 Schuster ............ A61B 10/0291
600/572

(Continued)

OTHER PUBLICATIONS

International Search Report and Written Opinion dated Jul. 27, 2015 for Application No. PCT/US2015/028429.

(Continued)

*Primary Examiner* — Max Hindenburg
(74) *Attorney, Agent, or Firm* — Frost Brown Todd LLC

(57) ABSTRACT

A biopsy system comprises an introducer and a biopsy device. The introducer comprises a cannula and at least two leaves. The cannula comprises an ovular cross-section, an open distal end and an open proximal end. The ovular cross-section defines a lumen extending between the open distal end and the open proximal end. The ovular cross-section of the cannula includes at least two flat sides. The at least two leaves extend distally from the open distal end. At least a portion of each of the at least two leaves extend from a respective flat side of the at least two flat sides of the cannula. The biopsy device comprises a body and an elongate needle. The elongate needle extends distally from the body. The elongate needle includes an ovular cross-section defining two straight sides. The cannula of the introducer is configured to slidably receive the elongate needle of the biopsy device.

20 Claims, 25 Drawing Sheets

(51) Int. Cl.
*A61B 17/34* (2006.01)
*A61B 90/00* (2016.01)

(52) U.S. Cl.
CPC .......... *A61B 17/34* (2013.01); *A61B 17/3415* (2013.01); *A61B 17/3421* (2013.01); *A61B 2010/0208* (2013.01); *A61B 2090/3908* (2016.02); *A61B 2090/3925* (2016.02)

(58) Field of Classification Search
CPC ........ A61B 2010/0208; A61B 17/3415; A61B 17/3421
USPC ........................................................ 600/572
See application file for complete search history.

(56) References Cited

U.S. PATENT DOCUMENTS

| | | | |
|---|---|---|---|
| 5,129,402 A * | 7/1992 | Koll | A61B 10/04 600/572 |
| 5,271,414 A * | 12/1993 | Partika | A61B 10/0266 600/567 |
| 5,526,822 A | 6/1996 | Burbank et al. | |
| 5,560,373 A | 10/1996 | De Santis | |
| 6,086,544 A | 7/2000 | Hibner et al. | |
| 6,228,055 B1 | 5/2001 | Foerster et al. | |
| 6,352,513 B1 * | 3/2002 | Anderson | A61B 10/0045 600/569 |
| 6,371,904 B1 | 4/2002 | Sirimanne et al. | |
| 6,626,849 B2 | 9/2003 | Huitema et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,229,417 B2 | 6/2007 | Foerster et al. | |
| 7,442,171 B2 | 10/2008 | Stephens et al. | |
| 7,465,279 B2 | 12/2008 | Beckman et al. | |
| 7,507,210 B2 | 3/2009 | Hibner et al. | |
| 7,854,706 B2 | 12/2010 | Hibner | |
| 7,988,642 B2 | 8/2011 | Hardin et al. | |
| 8,206,316 B2 | 6/2012 | Hibner et al. | |
| 8,371,443 B2 | 2/2013 | Nock et al. | |
| 8,376,957 B2 | 2/2013 | Hibner et al. | |
| 8,532,747 B2 | 9/2013 | Nock et al. | |
| 8,532,748 B2 | 9/2013 | Leimbach et al. | |
| 8,702,623 B2 | 4/2014 | Parihar et al. | |
| 8,764,680 B2 | 7/2014 | Rhad et al. | |
| 9,017,343 B2 * | 4/2015 | Westerling, Jr. | A61B 10/0266 606/133 |
| 9,282,948 B2 * | 3/2016 | Melchiorri | A61B 10/0266 |
| 9,414,815 B2 * | 8/2016 | Miller | A61B 10/025 |
| 9,414,816 B2 * | 8/2016 | Rhad | A61B 10/0275 |
| 2006/0074345 A1 | 4/2006 | Hibner | |
| 2008/0214955 A1 | 9/2008 | Speeg et al. | |
| 2009/0209854 A1 | 8/2009 | Parihar et al. | |
| 2010/0114031 A1 | 5/2010 | Jarial et al. | |
| 2010/0152610 A1 | 6/2010 | Parihar et al. | |
| 2010/0160819 A1 | 6/2010 | Parihar et al. | |
| 2011/0071391 A1 | 3/2011 | Speeg | |
| 2011/0071423 A1 | 3/2011 | Speeg et al. | |
| 2012/0010527 A1 | 1/2012 | Sundheimer et al. | |
| 2012/0059247 A1 | 3/2012 | Speeg et al. | |
| 2012/0065542 A1 | 3/2012 | Hibner et al. | |
| 2012/0330186 A1 | 12/2012 | Rhad et al. | |

OTHER PUBLICATIONS

Australian Office Action dated Dec. 5, 2016 for Application No. 2015253114, 2 pages.

* cited by examiner

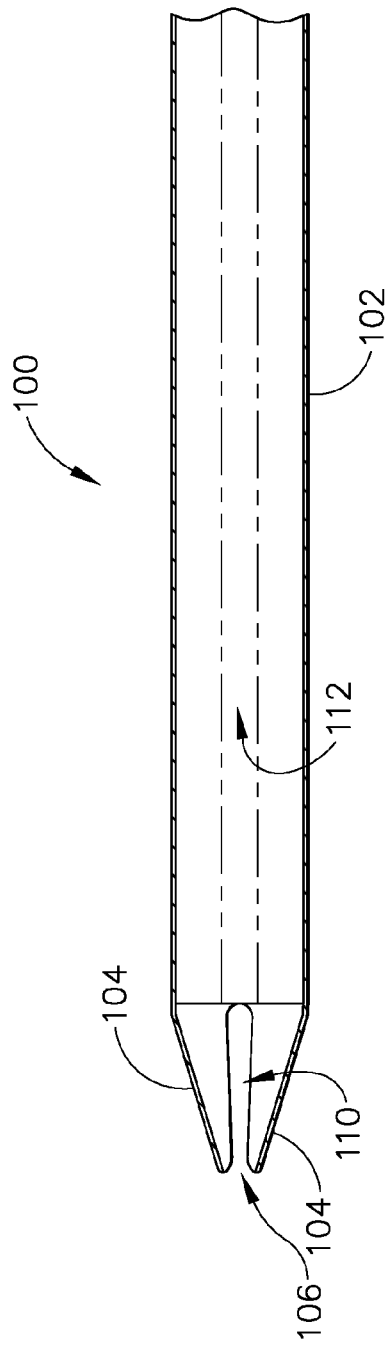
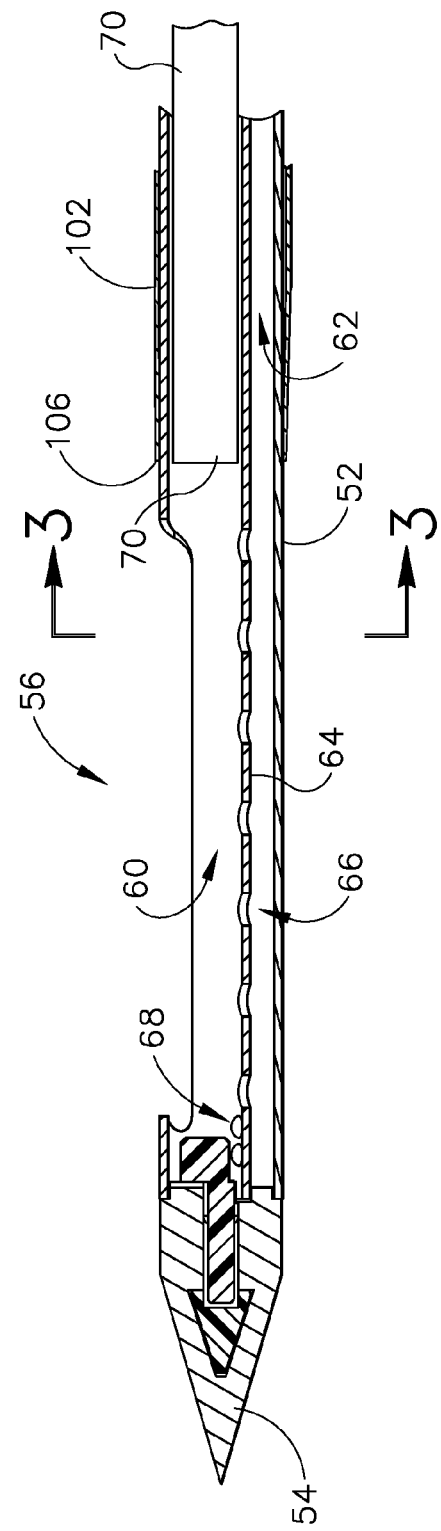

INTRODUCER FOR BIOPSY DEVICE

BACKGROUND

Biopsy samples have been obtained in a variety of ways in various medical procedures using a variety of devices. Biopsy devices may be used under simple visual guidance, palpatory guidance, stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pat. No. 7,507,210, entitled "Biopsy Cannula Adjustable Depth Stop," issued Mar. 24, 2009; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0317997, entitled "Tetherless Biopsy Device with Reusable Portion," published Dec. 16, 2010; and U.S. Pat. No. 8,764,680, entitled "Handheld Biopsy Device with Needle Firing," issued Jul. 1, 2014. The disclosure of each of the above-cited U.S. patents, U.S. patent application Publications, and U.S. Non-Provisional patent applications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK®, MICROMARK®, and CORMARK® brand devices from Devicor Medical Products, Inc. of Cincinnati, Ohio. Further exemplary devices and methods for marking a biopsy site are disclosed in U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pub. No. 2011/0071423, entitled "Flexible Biopsy Marker Delivery Device," published Mar. 24, 2011; U.S. Pub. No. 2011/0071424, entitled "Biopsy Marker Delivery Device," published Mar. 24, 2011; U.S. Pub. No. 2011/0071391, entitled "Biopsy Marker Delivery Device with Positioning Component," published Mar. 24, 2011; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; and U.S. Pat. No. 7,465,279, entitled "Marker Device and Method of Deploying a Cavity Marker Using a Surgical Biopsy Device," issued Dec. 16, 2008. The disclosure of each of the above-cited U.S. patents and U.S. patent application Publications is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 2A depicts a partial, side cross-sectional view of the introducer cannula of FIG. 1A;

FIG. 2B depicts a partial, side cross-sectional view of the needle of the biopsy device and the introducer cannula of FIG. 1A, with the needle of the biopsy device inserted in the introducer cannula;

Figure 1A:
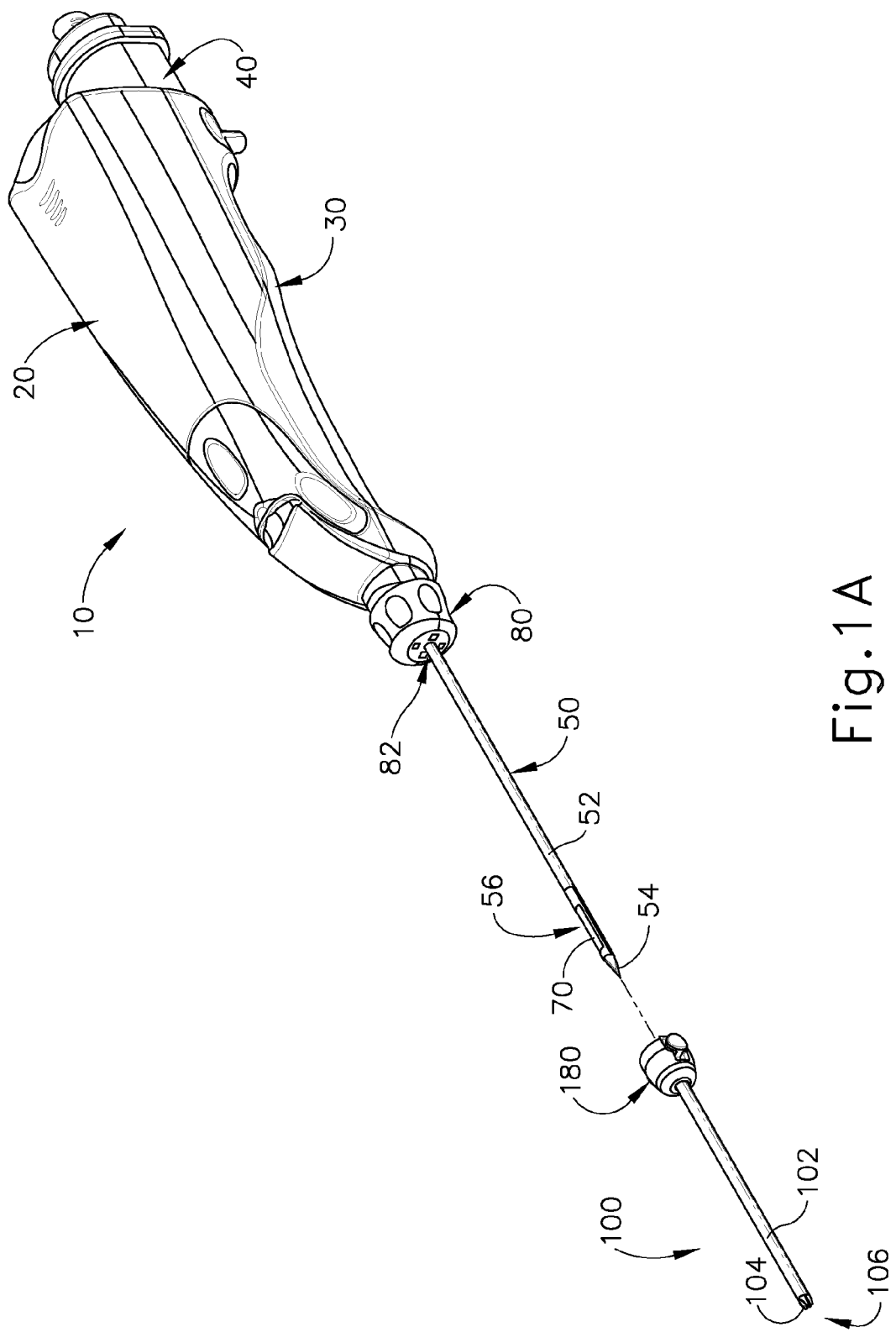
FIG. 1A depicts a perspective view of an exemplary biopsy device and an exemplary introducer cannula, with the introducer cannula separated from the biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary Biopsy Device

Figure 1B:
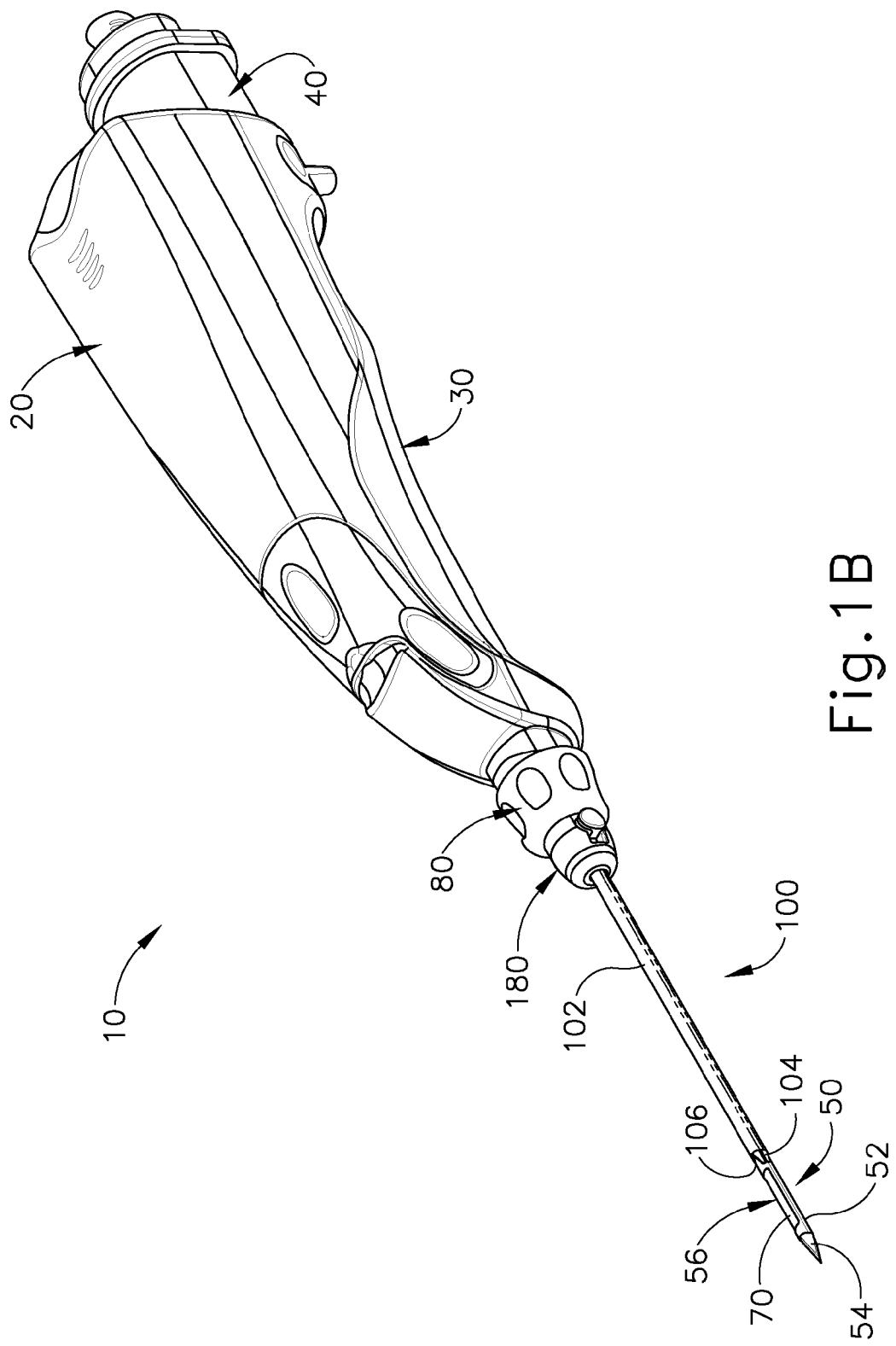
FIG. 1B depicts a perspective view of the biopsy device and introducer cannula of FIG. 1A, with the needle of the biopsy device inserted in the introducer cannula.

FIGS. 1A and 1B show an exemplary biopsy device (10). Biopsy device (10) of this example comprises a probe (30) and a holster (20). A needle (50) extends distally from probe (30), and is inserted into a patient's tissue to obtain tissue samples as will be described in greater detail below. These tissue samples are deposited in a tissue sample holder (40) at the proximal end of probe (30), as will also be described in greater detail below. Probe (30) is removably coupled with holster (20) in the present example. It should be understood that the use of the term "holster" herein should not be read as requiring any portion of probe (30) to be inserted into any portion of holster (20). A variety of types of structures, components, features, etc. (e.g., bayonet mounts, latches, clamps, clips, snap fittings, etc.) may be used to provide removable coupling of probe (30) and holster (20). Furthermore, in some biopsy devices (10), probe (30) and holster (20) may be of unitary or integral construction, such that the two components cannot be separated. By way of example only, in versions where probe (30) and holster (20) are provided as separable components, probe (30) may be provided as a disposable component, while holster (20) may be provided as a reusable component. Still other suitable structural and functional relationships between probe (30) and holster (20) will be apparent to those of ordinary skill in the art in view of the teachings herein.

Needle (50) of the present example includes a cannula (52), a piercing tip (54), a lateral aperture (56) located proximal to tip (54), and a hub member (80). Tissue piercing tip (54) is configured to pierce and penetrate tissue, without requiring a high amount of force, and without requiring an opening to be pre-formed in the tissue prior to insertion of tip (54). Alternatively, tip (54) may be blunt (e.g., rounded, flat, etc.) if desired. Tip (54) may also be configured to provide greater echogenicity than other portions of needle (50), providing enhanced visibility of tip (54) under ultrasound imaging. By way of example only, tip (54) may be configured in accordance with any of the teachings in U.S. Pat. Pub. No. 2012/0059247, entitled "Echogenic Needle for Biopsy Device," published Mar. 8, 2012, the disclosure of which is incorporated by reference herein. Other suitable configurations that may be used for tip (54) will be apparent to those of ordinary skill in the art in view of the teachings herein.

Figure 3:
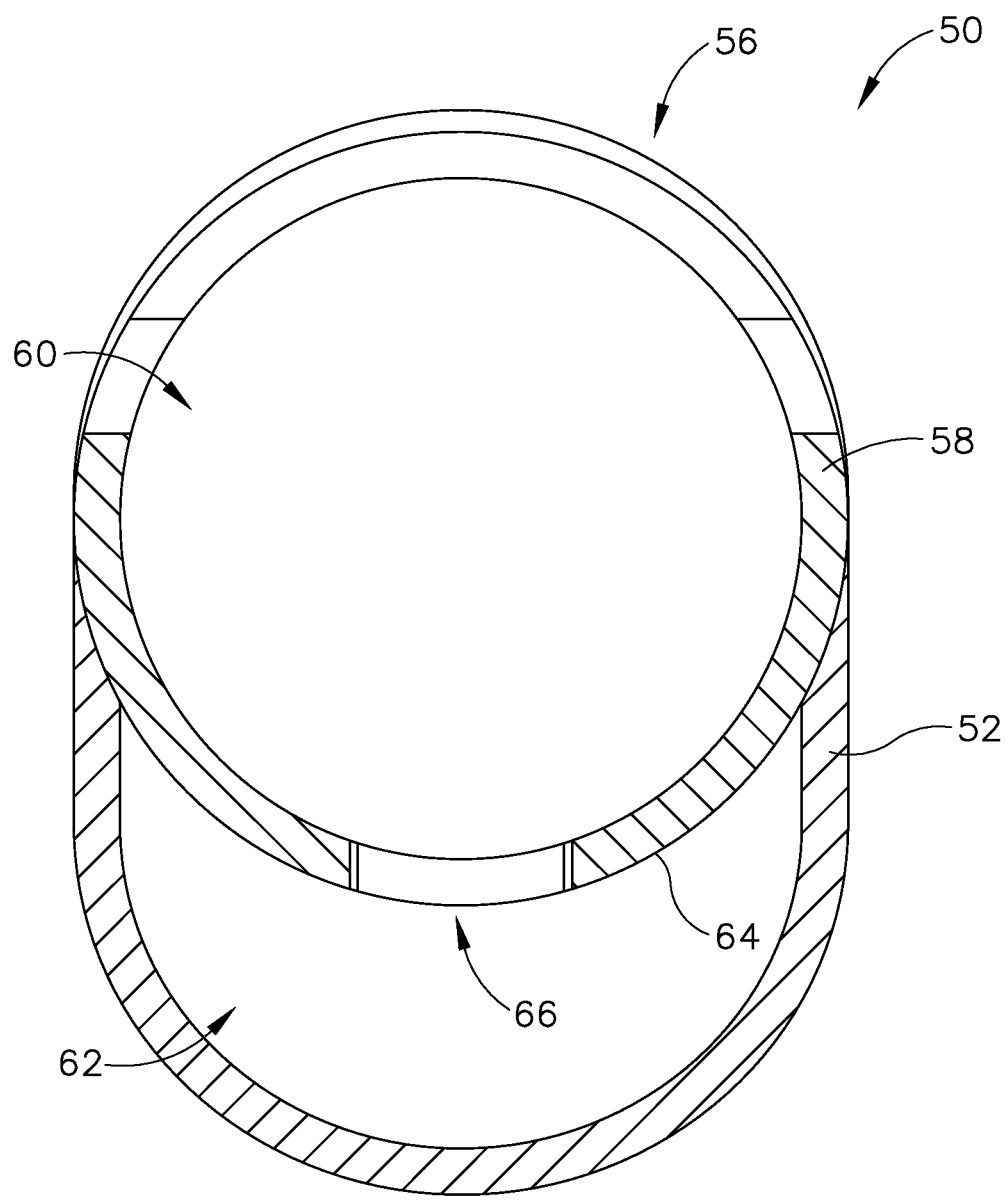
FIG. 3 depicts a front cross-sectional view of the needle of the biopsy device of FIG. 1A.

Lateral aperture (56) is sized to receive prolapsed tissue during operation of biopsy device (10). A hollow tubular cutter (70) having a sharp distal edge (not shown) is located within a first lumen (60) (as shown in FIG. 3) of needle (50). Cutter (70) is operable to rotate and translate relative to needle (50) and past lateral aperture (56) to sever a tissue sample from tissue protruding through lateral aperture (56). For instance, cutter (70) may be moved from an extended position (FIGS. 1A-1B) to a retracted position where the distal end of the cutter is just proximal of the proximal end of the lateral aperture (56) (FIG. 2B), thereby "opening" lateral aperture (56) to allow tissue to protrude therethrough; then from the retracted position back to the extended position to sever the protruding tissue. Mechanical components in holster (20) and probe (30) may cooperate to provide such actuation of cutter (70), as described in any reference cited herein or otherwise. As another merely illustrative example, cutter (70) may be actuated pneumatically in addition to or in lieu of being actuated by mechanical components. Other suitable alternative versions, features, components, configurations, and functionalities for providing cutter actuation will be apparent to those of ordinary skill in the art in view of the teachings herein.

While lateral aperture (56) is shown oriented in an upward position in FIG. 1A, it should be understood that needle (50) may be manually rotated to orient lateral aperture (56) at any desired angular position about the longitudinal axis of needle (50). Such rotation of needle (50) is facilitated in the present example by hub member (80). Hub member (80)

may be constructed and operable in accordance with the teachings of U.S. Pat. No. 8,764,680 and/or in any other suitable fashion. Various other suitable ways in which manual rotation of needle (50) may be provided will be apparent to those of ordinary skill in the art in view of the teachings herein. It should also be understood that rotation of needle (50) may be automated in various ways, including but not limited to the various forms of automatic or mechanized needle rotation described in various references that are cited herein.

As best seen in FIG. 2B, needle (50) also includes a longitudinal wall (64) extending proximally from the proximal portion of tip (54). While wall (64) does not extend along the full length of needle (50) in this example, it should be understood that wall (64) may extend the full length of needle (50) if desired. Wall (64) defines a second lumen (62) that is lateral to and parallel to cutter (70). Wall (64) includes a plurality of openings (66) that provide fluid communication between second lumen (62) and first lumen (60), as well as fluid communication between second lumen (62) and the lumen (not shown) of cutter (70). For instance, second lumen (62) may selectively provide atmospheric air to vent the lumen of cutter (70) during operation of biopsy device (10). Openings (66) are arranged such that at least one opening (68) is located at a longitudinal position that is distal to the distal edge of lateral aperture (56). Thus, the lumen of cutter (70) and second lumen (62) may remain in fluid communication even when cutter (70) is advanced to a position where the distal cutting edge of cutter (70) is located at a longitudinal position that is distal to the longitudinal position of the distal edge of lateral aperture (56). Of course, as with any other component described herein, any other suitable configurations may be used.

Figure 4:
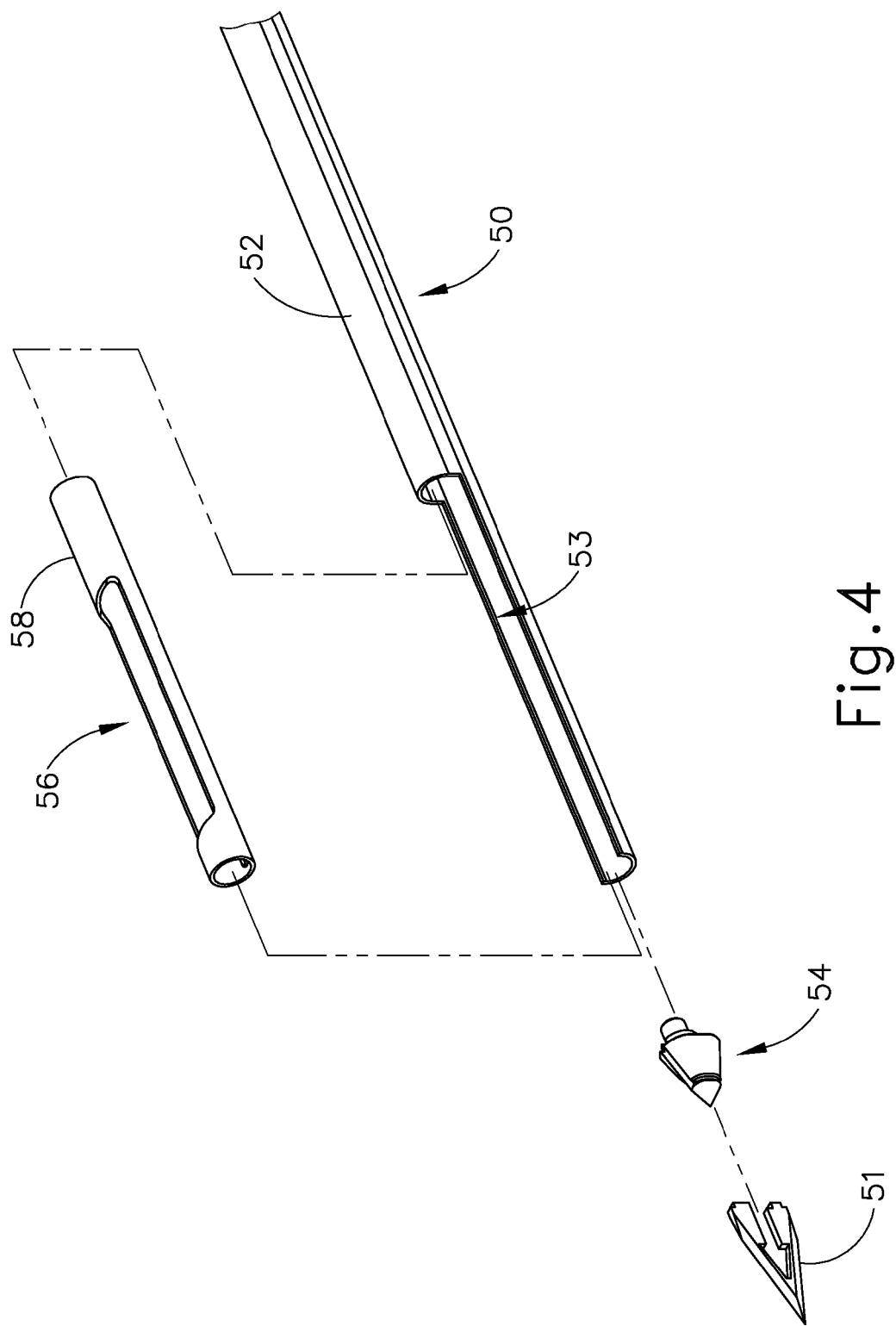
FIG. 4 depicts a partial exploded view of the needle of the biopsy device of FIG. 1A.
Figure 5:
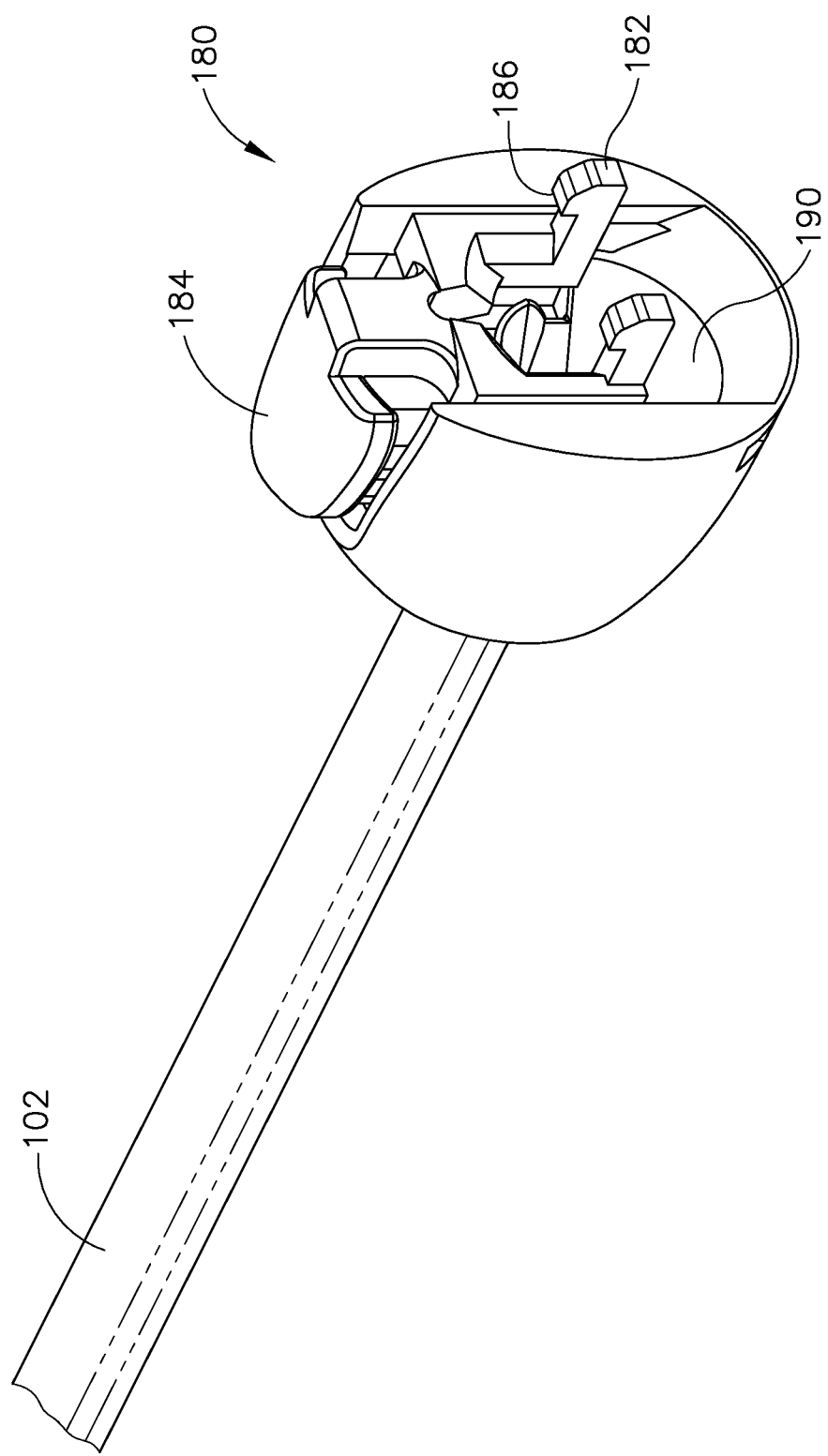
FIG. 5 depicts a partial perspective view of the proximal portion of the introducer cannula of FIG. 1A.
Figure 6:
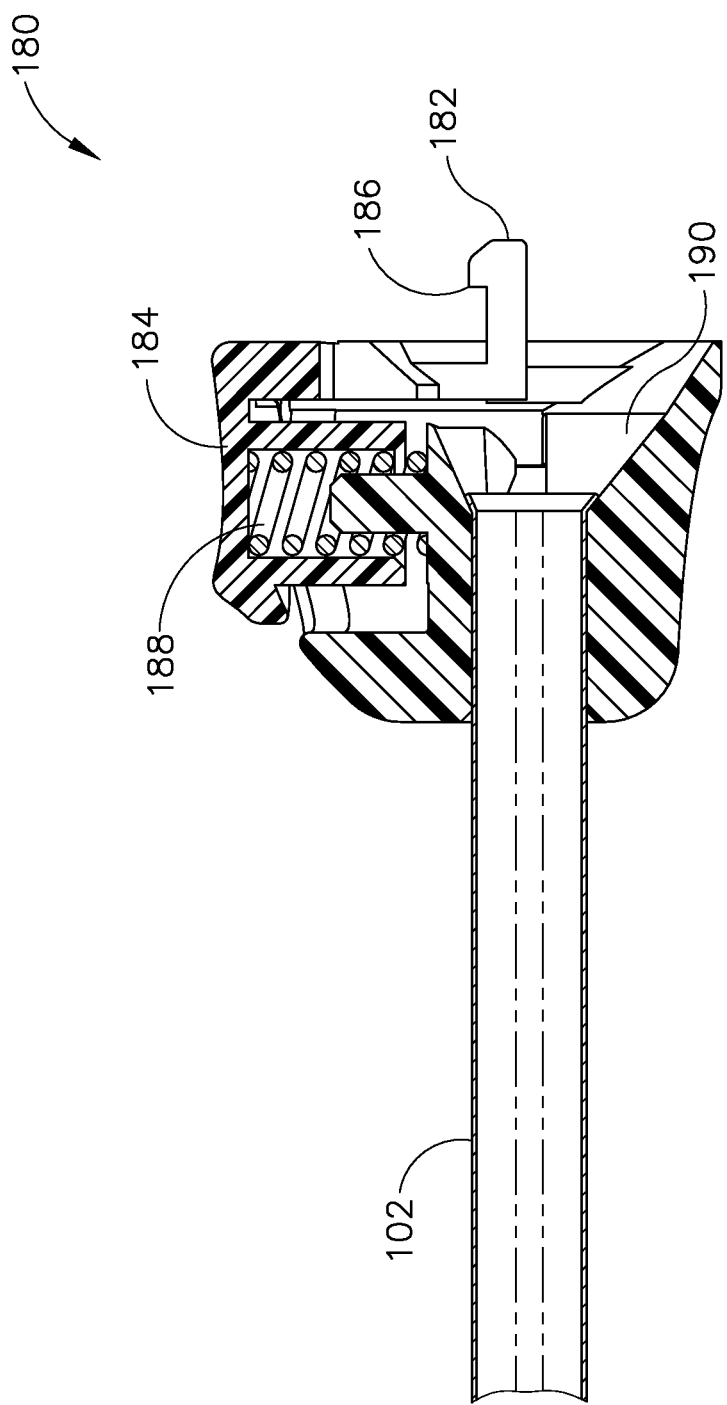
FIG. 6 depicts a side cross-sectional view of the proximal portion of the introducer cannula of FIG. 5.
Figure 7A:
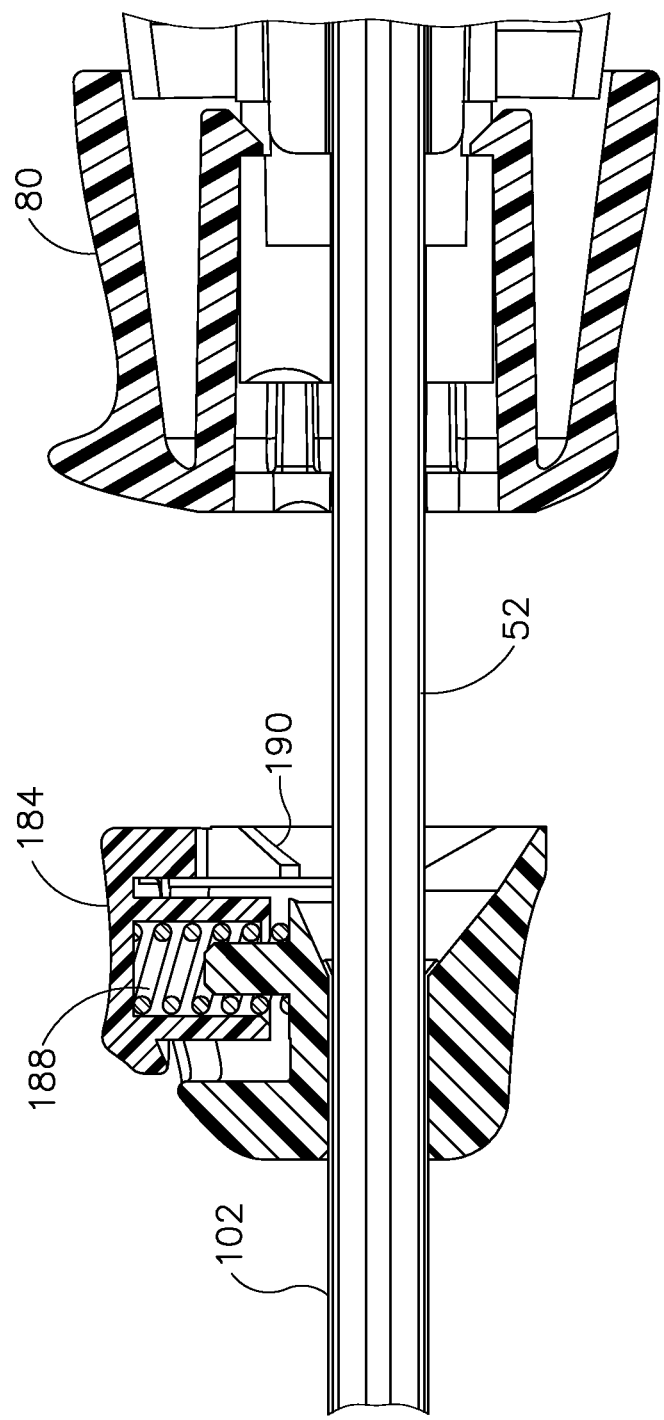
FIG. 7A depicts a side cross-sectional view of the needle of the biopsy device of FIG. 1A partially inserted into the introducer of FIG. 5.
Figure 7B:
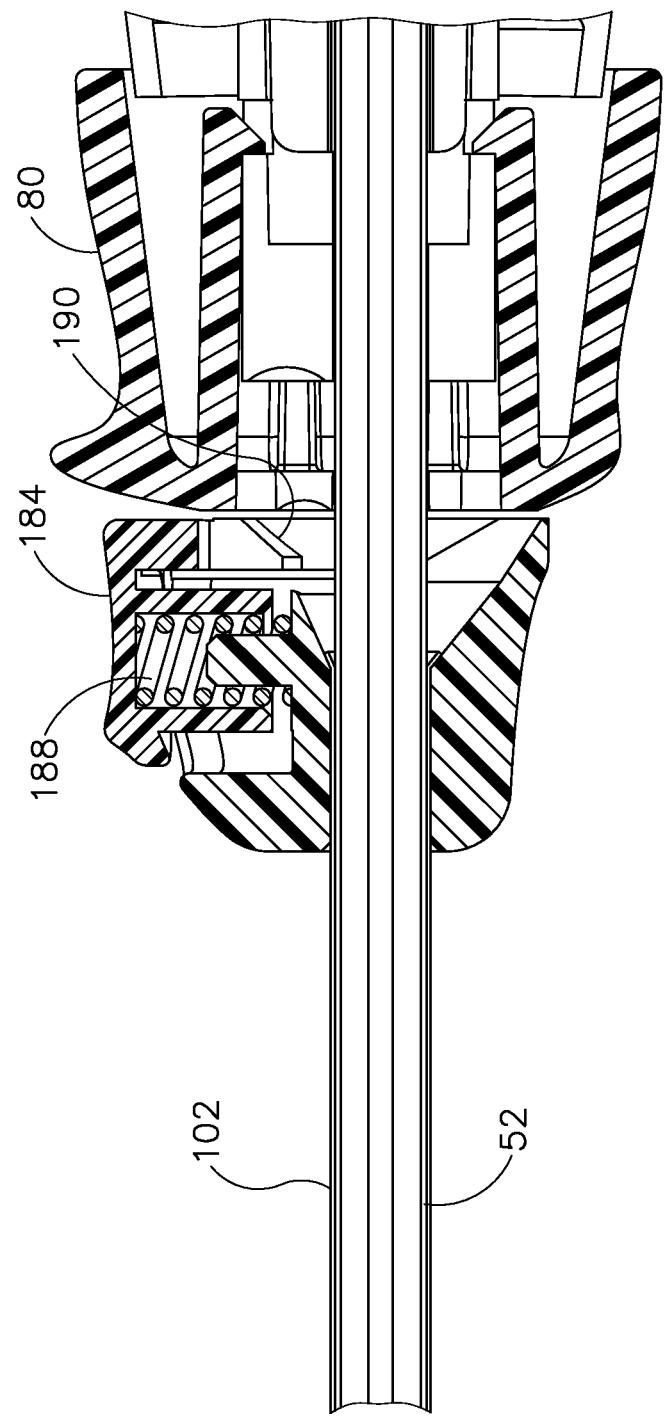
FIG. 7B depicts a side cross-sectional view of the needle of the biopsy device of FIG. 1A partially inserted into the introducer of FIG. 5.

FIG. 3 shows a cross sectional view of needle (50) taken at line 3-3 of FIG. 2B. As can be seen, needle (50) has a non-circular cross-sectional shape such as, a generally ovular shape defined by cannula (52). In the present example, longitudinal wall (64) is formed by an internal tube (58) which also forms lateral aperture (56). As can best be seen in FIG. 4, tube (58) is inserted into a cut out portion (53) in cannula (52). Tube (58) may be fixed to cannula (52) by any suitable means such as laser welding, adhesive bonding, or the like.

Probe (30) may also include a valve assembly in fluid communication with at least part of needle (50), selectively changing a pneumatic state of at least part of needle (50) based on any suitable conditions such as the longitudinal position of cutter (70). For instance, such a valve assembly may selectively change the pneumatic state of second lumen (62). Such a valve assembly may be constructed in accordance with the teachings of U.S. Pub. No. 2010/0317997; in accordance with the teachings of U.S. Pat. No. 8,764,680; and/or otherwise. In addition or in the alternative, valving may be provided by a vacuum source and/or a vacuum canister, such as is taught in U.S. Pub. No. 2008/0214955. Other suitable alternative versions, features, components, configurations, and functionalities of needle (50) will be apparent to those of ordinary skill in the art in view of the teachings herein.

Tissue sample holder (40) of the present example is configured to receive tissue samples that are severed by cutter (70) and communicated proximally through the hollow interior of cutter (70). Tissue sample holder (40) may include one or more removable trays (not shown) that permit a user to remove severed tissue samples from tissue sample holder (40) without having to remove tissue sample holder (40) from probe (30). In some such versions, tissue sample holder (40) is constructed in accordance with the teachings of U.S. Patent Pub. No. 2012/0065542, entitled "Biopsy Device Tissue Sample Holder with Removable Tray," filed Mar. 15, 2012, the disclosure of which is incorporated by reference herein. In addition or in the alternative, tissue sample holder (130) may include a rotatable manifold (not shown) that is in fluid communication with a vacuum source and cutter (70); and that is rotatable to successively index separate tissue receiving chambers to cutter (70). By way of example only, tissue sample holder (40) may be constructed and operable in accordance with the teachings of U.S. Pub. No. 2008/0214955, the disclosure of which is incorporated by reference herein. As another merely illustrative example, tissue sample holder (40) may be constructed and operable in accordance with the teachings of U.S. Pub. No. 2010/0160824, entitled "Biopsy Device with Discrete Tissue Chambers," published Jun. 24, 2010, the disclosure of which is incorporated by reference herein. Still other suitable ways in which tissue sample holder (40) may be constructed and operable will be apparent to those of ordinary skill in the art in view of the teachings herein.

Biopsy device (10) may also include a vacuum source (not shown), such as a vacuum pump. By way of example only, a vacuum source may be incorporated into probe (30), incorporated into holster (20), and/or be a separate component altogether. In versions where a vacuum source is separate from probe (30) and holster (20), the vacuum source may be coupled with probe (30) and/or holster (20) via one or more conduits such as flexible tubing. It should also be understood that a vacuum source may be in fluid communication with tissue sample holder (40) and needle (50). Thus, the vacuum source may be activated to draw tissue into lateral aperture (56) of needle (50). Tissue sample holder (40) is also in fluid communication with cutter (70) in the present example. A vacuum source may thus also be activated to draw severed tissue samples through the hollow interior of cutter (70) and into tissue sample holder (40). In some versions, a vacuum source is provided in accordance with the teachings of U.S. Pub. No. 2008/0214955. In addition or in the alternative, a vacuum source may be provided in accordance with the teachings of U.S. Pat. No. 8,764,680. As yet another merely illustrative example, a vacuum source may be provided in accordance with the teachings of U.S. Pat. No. 8,376,957, entitled "Biopsy Device with Auxiliary Vacuum Source," issued Feb. 19, 2013, the disclosure of which is incorporated by reference herein. Still other suitable ways in which a vacuum source may be provided will be apparent to those of ordinary skill in the art in view of the teachings herein. It should also be understood that a vacuum source may simply be omitted, if desired.

Biopsy device (10) of the present example is sized and configured such that biopsy device (10) may be operated by a single hand of a user. In particular, a user may grasp biopsy device (10), insert needle (50) into a patient's breast, and collect one or a plurality of tissue samples from within the patient's breast, all with just using a single hand. Alternatively, a user may grasp biopsy device (10) with more than one hand and/or with any desired assistance. It should also be understood that biopsy device (10) may be configured to mount to a table or fixture, and be used under stereotactic guidance. Of course, biopsy device (10) may instead be used under ultrasound guidance, MRI guidance, PEM guidance, BSGI guidance, or otherwise. In some settings, the user may capture a plurality of tissue samples with just a single insertion of needle (50) into the patient's breast. Such tissue samples may be pneumatically deposited in tissue sample holder (40), and later retrieved from tissue sample holder (40) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Other suitable components, features, configurations, and operabilities for biopsy device (10) will be apparent to those of ordinary skill in the art in view of the teachings herein.

II. Exemplary Introducer Cannula with Open Distal End

In some settings, needle (50) is inserted directly into a patient's tissue, such that the outer surface of the entire inserted length of cannula (52) comes in direct contact with the patient's tissue. In some other versions, an introducer cannula is used. By way of example only, an introducer cannula having an open distal tip may first be inserted into the patient's tissue. In some instances, as will be described in greater detail below, an obturator having a sharp distal tip (that protrudes from the open distal end of the introducer cannula) may be disposed in the introducer cannula when the two are inserted into the patient's tissue. If an obturator is used during insertion into the patient's tissue, the obturator may be removed after the introducer cannula has reached a desired depth in the tissue. Needle (50) and/or other instruments may then be fed into the introducer cannula to reach the tissue at the distal end of the cannula.

In some settings, such as those where the needle of a biopsy device has a sharp tip, the introducer may be coupled with the needle before the two are inserted together into the patient's tissue. A merely illustrative example of this is shown in FIGS. 1A-2B. In particular, FIG. 1A shows biopsy device (10) and an exemplary introducer (100) before needle (50) of biopsy device (10) is inserted in introducer (100). FIG. 1B shows needle (50) inserted in introducer (100). As seen in FIGS. 1A-1B, introducer (100) of this example comprises a cannula (102), four distal leaves (104) at an open distal end (106), and a latching feature (180). Latching feature (180) is operable to selectively secure introducer (100) to biopsy device (10) as will be described in greater detail below. As seen in FIG. 2A, cannula (102) defines an internal lumen (112) that is in fluid communication with open distal end (106). As also seen in FIG. 2A, leaves (104) are resiliently biased to deflect slightly inwardly, yet a gap (110) is defined between leaves (104) to facilitate independent movement of leaves (104) toward or away from each other.

As can be seen in FIGS. 1B and 2B, when cannula (52) of needle (50) is fully inserted into lumen (112) of cannula (102), a distal portion of needle (50) protrudes distally from cannula (102). In particular, lateral lumen (56) is fully exposed, being positioned distal to open distal end (106) of cannula (102). As will be described in greater detail below, the outer diameter of cannula (52) is greater than the inner diameter defined between leaves (104) when leaves are in a relaxed state, such that cannula (52) deflects leaves (104) outwardly when cannula (52) is inserted in cannula (102). In particular, leaves (104) are deflected such that they are substantially aligned with proximal portions of the sidewall of cannula (102). Leaves (104) thus resiliently bear against cannula (52) of needle (50).

In an exemplary use, introducer (100) is coupled with needle (50) as shown in FIGS. 1B and 2B. With cutter (70) at a distal position to effectively close lateral aperture (56), introducer (100) and needle (50) are then inserted together into a patient's tissue. Tip (54) pierces and penetrates the patient's tissue during this insertion. Cutter (70) is then reciprocated to acquire one or more tissue samples, which are deposited into tissue sample holder (40) (e.g., using vacuum assistance, etc.). Once the desired number of tissue samples have been acquired, needle (50) is decoupled from introducer (100), and cannula (52) is withdrawn from cannula (102), leaving cannula (102) disposed in the patient's tissue. A marker (not shown) applier may then be inserted into lumen (112) of cannula (102) to deposit one or more markers at the biopsy site. In addition or in the alternative, one or more medicaments, brachytherapy pellets, and/or other substances may be applied at the biopsy site through lumen (112) of cannula (102). In addition or in the alternative, a variety of other kinds of instruments may be inserted through lumen (112) of cannula (102) to reach the biopsy site. Introducer (100) may then be pulled from the patient's tissue. Still other suitable ways in which introducer (100) may be used will be apparent to those of ordinary skill in the art in view of the teachings herein.

Introducer (100) of the present example is operable to selectively couple with biopsy device (10) through a latching feature (180). As best seen in FIGS. 5-7B, latching feature (180) of this example comprises a pair of latches (182) and an associated button (184). Latches (182) are received in complementary slots (82) of hub member (80) (as seen in FIG. 1A). Latches (182) include outward projections (186) that retain latches (182) in hub member (80). Latches (182) and button (184) are positioned on a spring (188), which resiliently bias latches (182) to the position shown in FIG. 6 yet allow latches (182) to be deflected downwardly to accommodate insertion in slots (82) of hub member (80). Spring (188) also allows button (184) to be pressed downwardly to decouple latches (182) from slots (82). As can also be seen in FIGS. 5-7B, the interior of latching feature (180) includes ramps (190) that help guide the distal end of cannula (52) into lumen (112) of introducer (100). While not shown, it should be understood that introducer (100) may include one or more internal valves or seals, such as to reduce or prevent leakage of bodily fluids from introducer (100), particularly when needle (50) is removed from introducer (100) while introducer (100) remains inserted in tissue. It should also be understood that an introducer (100) may selectively couple with a biopsy device (10) in various other ways. Other suitable variations for latching feature (180) will be apparent to those of ordinary skill in the art in view of the teachings herein. Furthermore, introducer (100) need not necessarily be securable to biopsy device (10), such that latching feature (180) and variations thereof may simply be omitted if desired.

Figure 8:
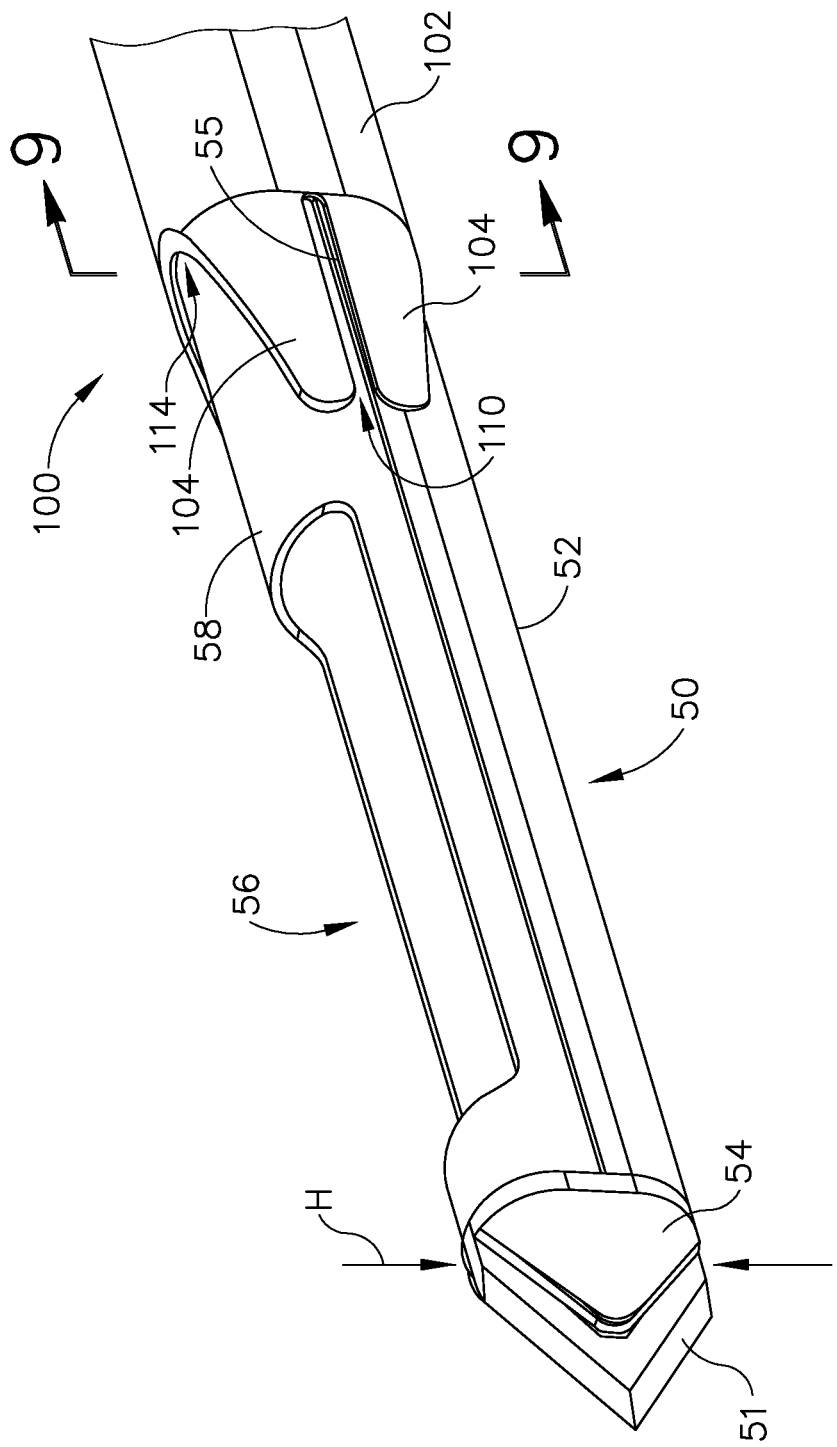
FIG. 8 depicts a perspective view of a distal end of the introducer of FIG. 1A with the needle of the biopsy device of FIG. 1A fully inserted into the introducer.

FIG. 8 shows a detailed view of the distal end of introducer (100) with needle (50) fully inserted into introducer (100). In particular, leaves (104) are shown engaging the side of needle (50). As described above, needle (50) of the present example has a non-circular, ovular cross-section with relatively flat sides. Accordingly, each leaf (104) may engage a portion of the relatively flat surface of needle (50), such as with a slight interference fit. Yet, gap (110) permits the leaves to avoid contact with a seam (55) between tube (58) and cannula (52) of needle (50). In some examples, the interference between needle (50) and leaves (104) may be 0.011 inches, although the interference may range from 0.005 inches to 0.02 inches. Of course any other suitable amount of interference may be used as will be apparent to those of ordinary skill in the art in view of the teachings herein.

Figure 9:
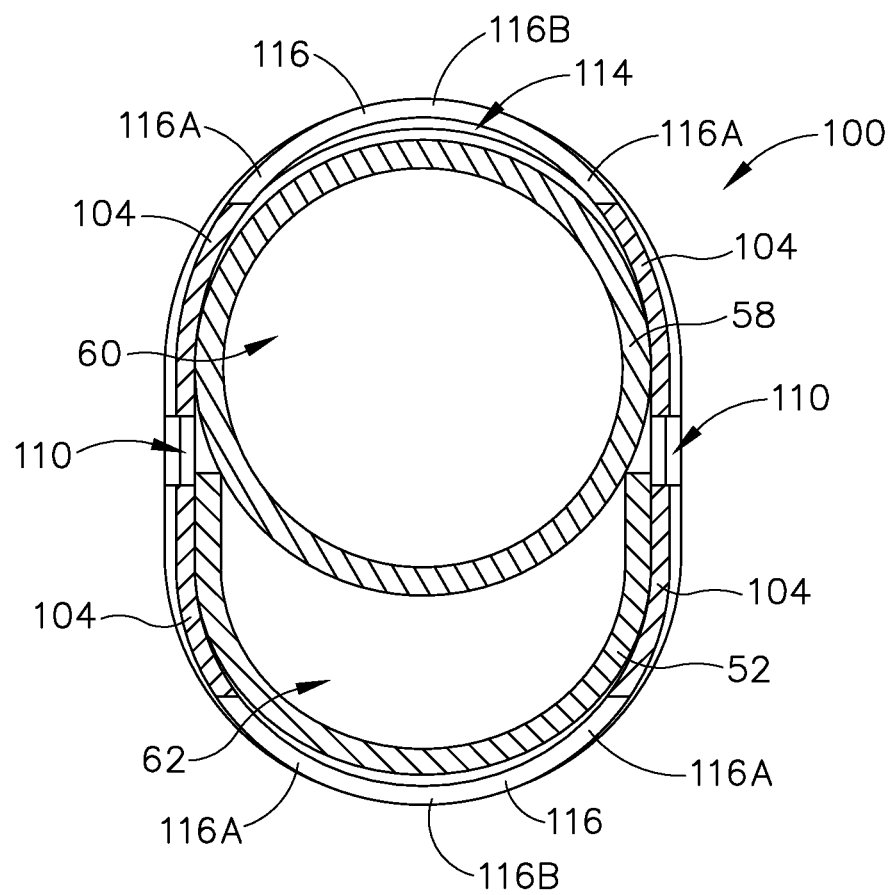
FIG. 9 depicts a front cross-sectional view of the introducer and needle of FIG. 8 with the cross section taken along line 9-9 of FIG. 8.

As can be seen in FIGS. 8 and 9, the region of introducer cannula (102) that is proximal to leaves (104) may have a cross-sectional shape corresponding to the cross-sectional shape of needle (50). Additionally, the region of introducer cannula (102) that is proximal to leaves (104) may be configured to create a slight gap or clearance opening (114) between cannula (102) and cannula (52) of needle (50) at the top and bottom of needle (50). As can best be seen in FIG. 9, opening (114) is disposed at the top and bottom of introducer (100) and is defined by introducer (100) and needle (50). Opening (114) provides a clearance space to permit introducer cannula (102) to clear tip (54), particularly if tip (54) is sized slightly larger relative to the major outer diameter of needle cannula (52), or if a portion of the tip extends slightly above the top surface of the cannula (52) and/or a portion of the tip extends slightly below the bottom surface of the cannula (52). For instance, in some examples needle (50) has an oversized tissue piercing tip (54). Alternatively tip (54) is offset to extend above or below cannula (52). Consequently, opening (114) is configured to accommodate such examples, while still maintaining a relatively tight fit between introducer (100) and needle (50). Of course, in other examples opening (114) may be omitted entirely.

Figure 10:
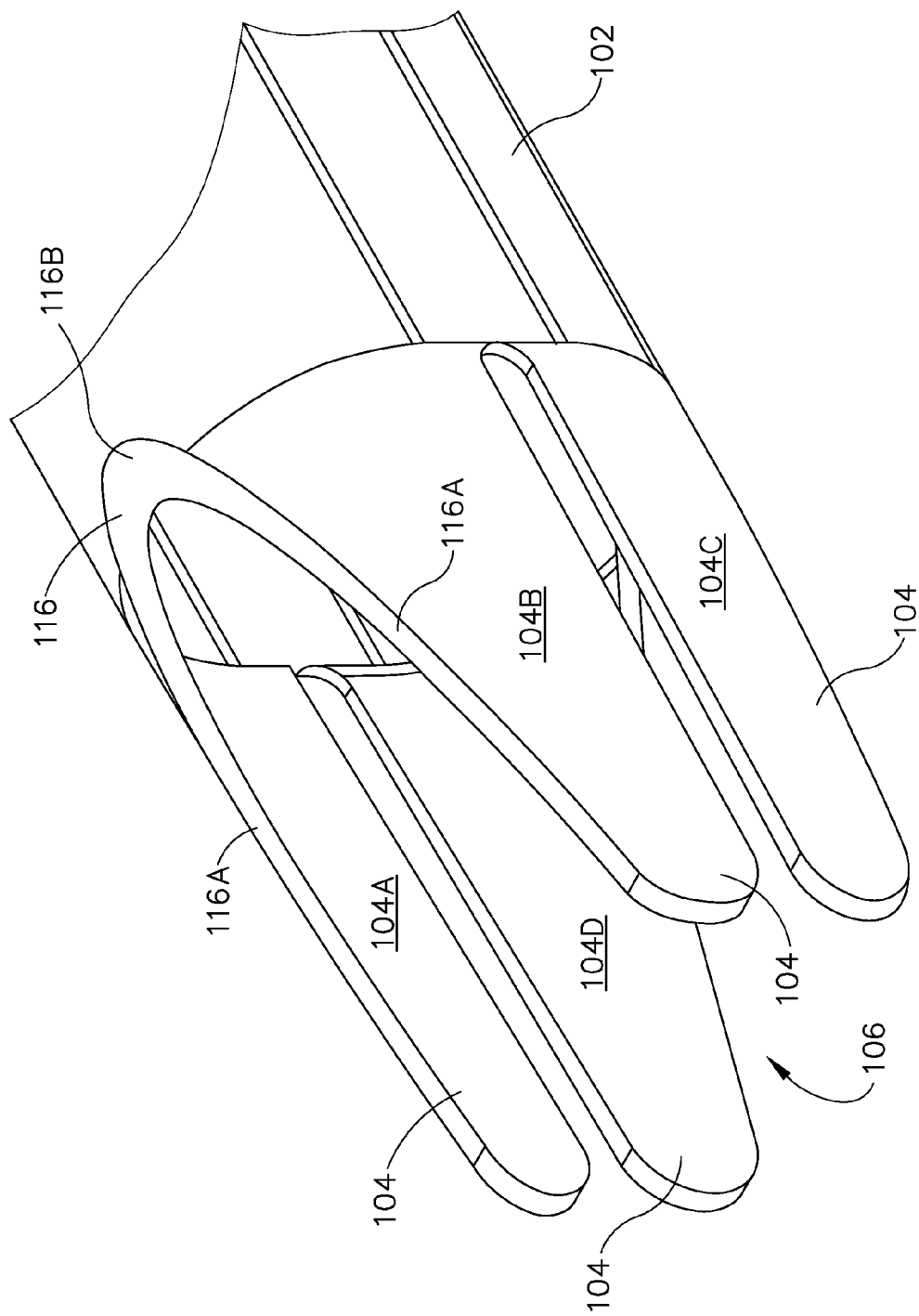
FIG. 10 depicts a partial perspective view of the distal end of the introducer of FIG. 1A.

FIG. 10 shows a detailed view of the distal end of introducer (100) without needle (50). As can be seen, in the example shown, the four leaves (104) are arranged in a symmetrical configuration, with two leaves (104A, 104B) associated with the top of cannula (102) and two leaves (104C, 104D) associated with the bottom of cannula (102). Leaves (104A, 104D) are associated with one side of cannula (102), and leaves (104B, 104C) are associated with the other side of cannula (102). In the embodiment shown, needle (50) may be inserted into introducer (100) in the orientation depicted or in an upside down orientation.

A chamfered surface (116) can be provided in association with a top portion of cannula (102), and a chamfered surface (116) can be provided in association with a bottom surface of cannula (102). In the embodiment shown, a chamfered surface (116) is provided in association with the upper edge portions of leaves (104A, 104B) and a distal portion of the top of cannula (102). The chamfered surface (116) may be formed by electrical discharge machining (EDM), grinding, or other suitable machining methods. The chamfered surface (116) shown in FIG. 10 includes portions (116A) associated with the upper edge portions of leaves (104A, 104B), and an apex portion (116B) associated with the top of cannula (102), extending partially into the top surface of cannula (102). Apex portion (116B) extends between and joins the chamfered surface portions (116A) formed on leaves (104A, 104B). Similarly, a second chamfered surface (116) can be provided in association with the bottom edge portions of leaves (104C, 104D) and a distal portion of the bottom of cannula (102). Such a configuration may permit introducer (100) more easily penetrate tissue thereby reducing the penetration force required when a user is inserting biopsy device (10) into a patient. In other versions, the size, angle, and/or shape of chamfered surface (116) may be varied as will be apparent to those of ordinary skill in the art in view of the teachings herein. Of course, in other examples such a feature may also be omitted entirely.

Leaves (104) are also shown as being resiliently biased inwardly. Thus, the distal ends of leaves (104) define an aperture having a geometry slightly smaller than the external geometry of needle (50), such as to provide a slight interference fit between the leaves (104) and the sides of needle (50). As described above, this resilient bias permits leaves (104) to engage the sides of needle (50) thus deflecting leaves (104) outwardly as needle (50) is inserted into introducer (100). Additionally, in some examples, leaves (104) may be tapered such that they decrease in thickness as they extend distally from introducer cannula (102). Such a taper may permit leaves (104) to more easily deflect tissue thereby reducing the penetration force required when inserting biopsy device (10) into a patient.

Figure 11:
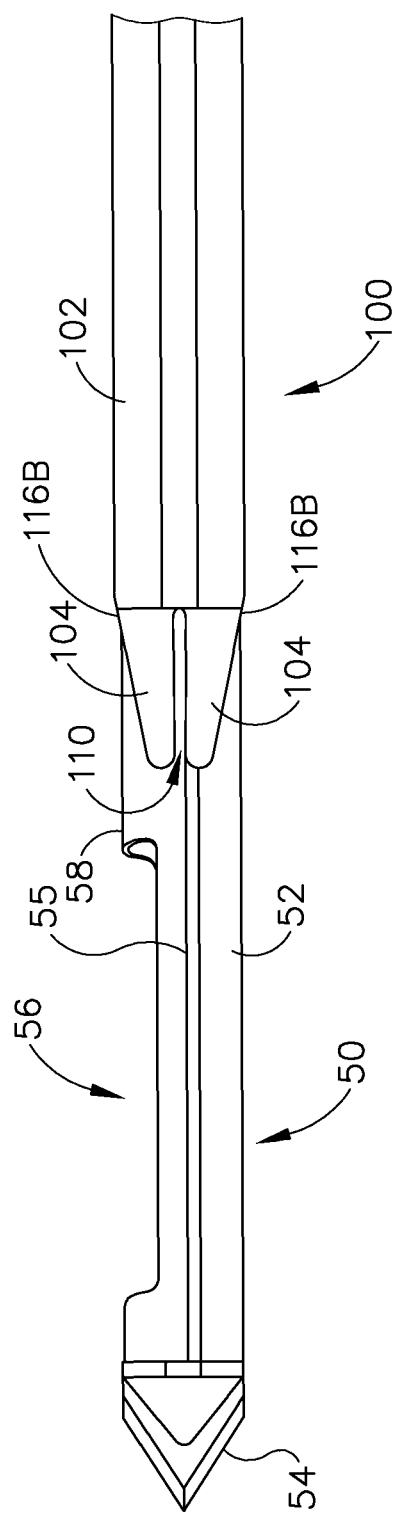
FIG. 11 depicts a side view of the needle of the biopsy device of FIG. 1A fully inserted into introducer of FIG. 5.
Figure 12:
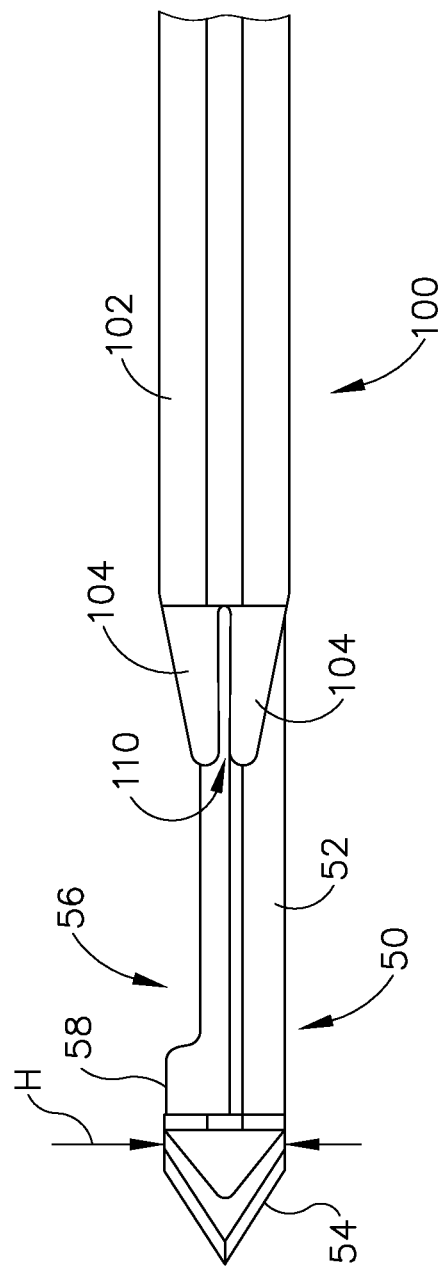
FIG. 12 depicts a side view of the needle of the biopsy device of FIG. 1A intermediately inserted into the introducer of FIG. 5.
Figure 13:
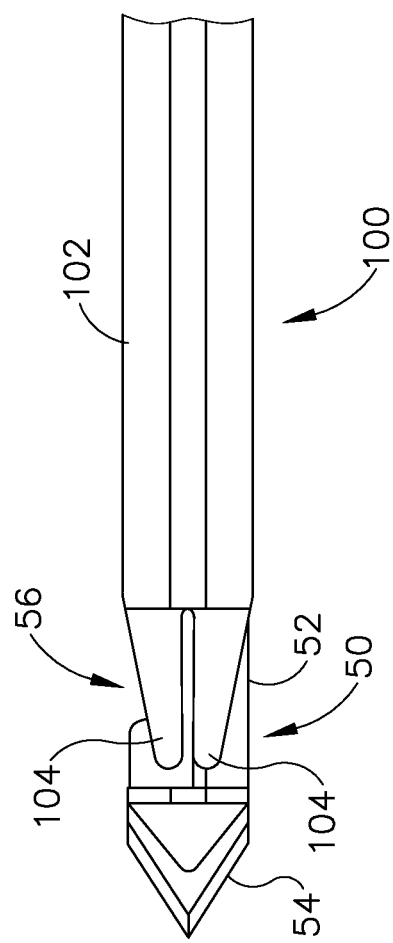
FIG. 13 depicts a side view of the needle of the biopsy device of FIG. 1A partially inserted into the introducer of FIG. 5.

FIGS. 11 through 13 show the progression of introducer (100) as needle (50) is removed (or inserted) from introducer (100). In particular, needle (50) moves from a fully inserted configuration shown in FIG. 11, to an intermediate insertion shown in FIG. 12, to a nearly removed insertion shown in FIG. 13. As can be seen, the seam (55) between cannula (52) and tube (58) of needle (50) is generally aligned with gap (110) of introducer (100). Accordingly, the distal ends of leaves (104) may avoid directly engaging the seam (55) between cannula (52) and tube (58) of needle (50). Such a configuration may prevent introducer (100) from catching on needle (100) as it is inserted onto, or removed from, needle (100).

In some examples, needle (100) may comprise an oversized tissue piercing tip (54). For instance, tissue piercing tip (54) may comprise a generally flat blade (51) having a height (H) greater than the major diameter (or major cross-sectional dimension as measured from top to bottom) of the outer surface of cannula (52). Openings (114), provided at the top and bottom of cannula (52) as described above, may provide additional clearance to permit introducer (100) to be inserted into (or retracted from) needle (50) without catching on tissue piercing tip (54). In one non-limiting example, openings (114) can be at least 0.002 inch measured along the major (vertical) axis of cannula (52), and in one embodiment openings (114) can be between 0.003 inch and 0.005 inch.

Figure 14:
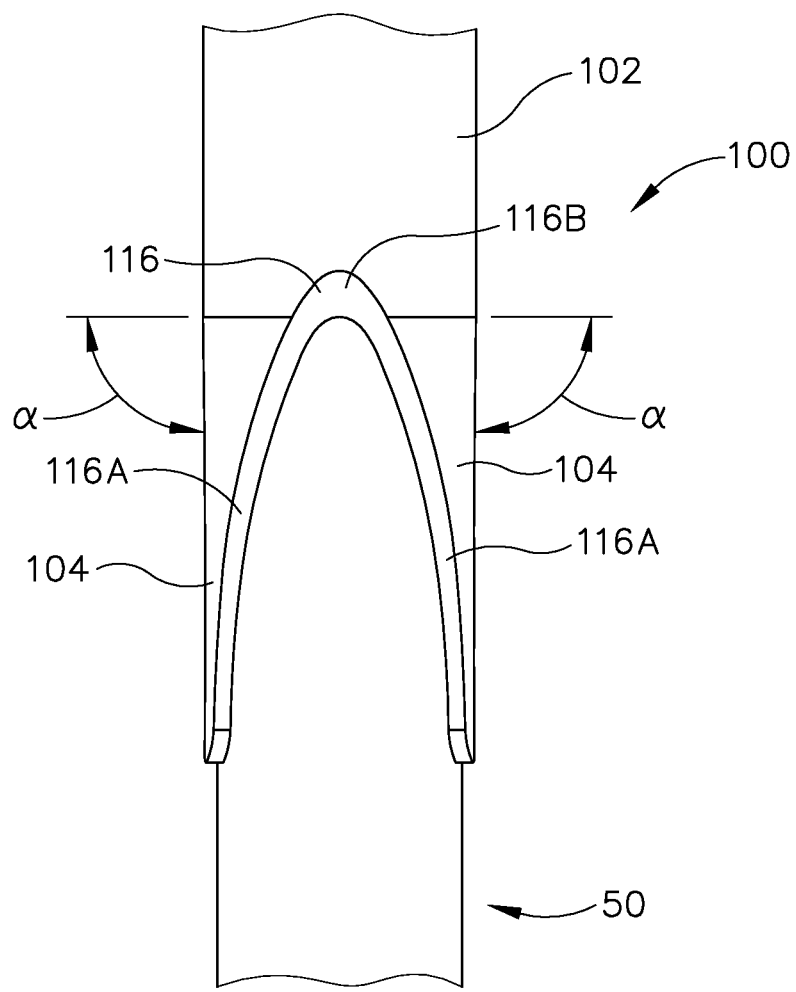
FIG. 14 depicts a partial top view of the needle of the biopsy device of FIG. 1A fully inserted into the introducer of FIG. 5.
Figure 15:
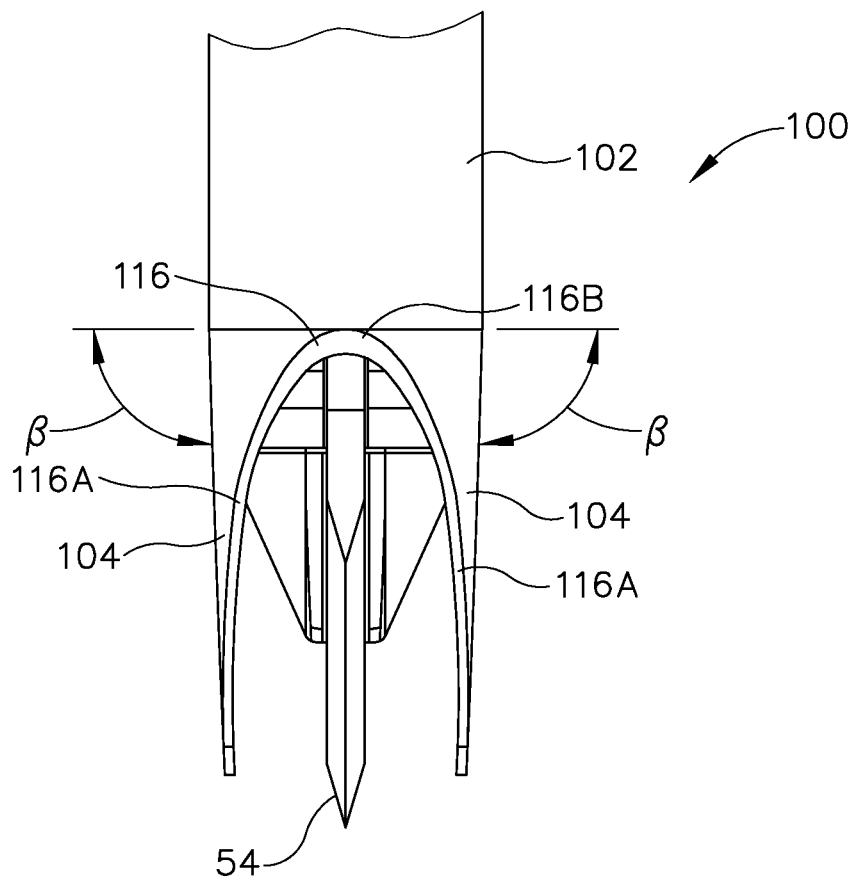
FIG. 15 depicts a partial top view of the needle of the biopsy device of FIG. 1A partially inserted into the introducer of FIG. 5.

FIGS. 14 and 15 show a top view of introducer (100) where leaves (104) are deflected by cannula (52) and relaxed, respectively. In the deflected state, leaves (104) are shown as having a deflected angle ($\alpha$) relative to a projection orthogonal to the longitudinal axis of introducer cannula (102). Similarly, in the relaxed state, leaves (104) are shown as having a relaxed angle ($\beta$) relative to a projection orthogonal to the longitudinal axis of introducer cannula (102). As can be seen by comparing FIGS. 14 and 15, deflected angle ($\alpha$) is smaller than relaxed angle ($\beta$). Thus, cannula (52) of needle (50) pushes leaves (104) angularly outward relative to introducer cannula (102). Although FIGS. 14 and 15 show angles ($\alpha$, $\beta$) as being slightly exaggerated for purposes of illustration, it should be understood that the difference between deflected angle ($\alpha$) and relaxed angle ($\beta$) may be any suitable amount that still permits deflection of leaves (104). Other leaf (104) configurations having different angles ($\alpha$, $\beta$) will be apparent to those of ordinary skill in the art in view of the teachings herein.

III. Exemplary Introducer Cannula with Two Distal Leaves

Figure 16:
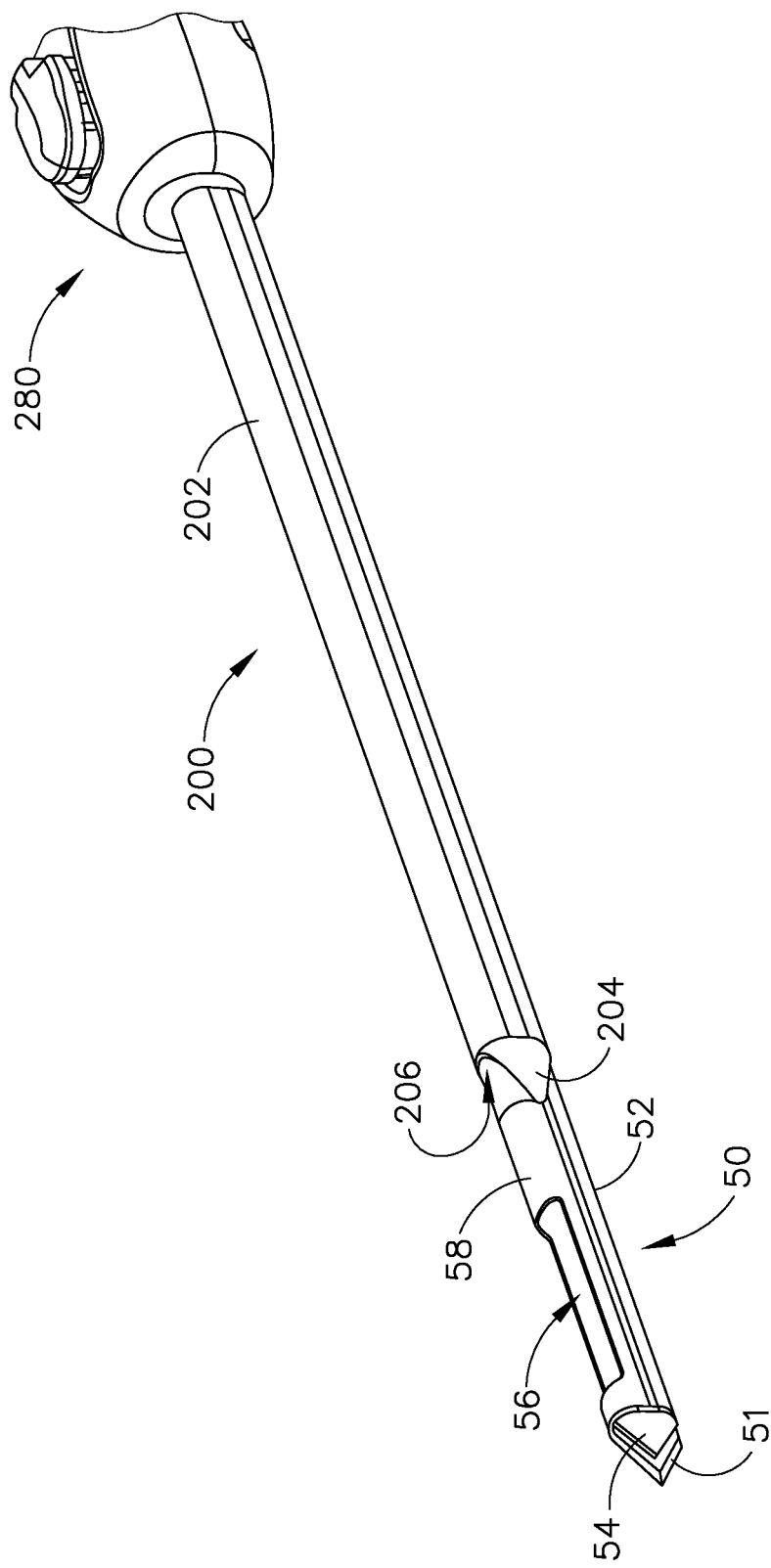
FIG. 16 depicts a perspective view of an exemplary alternative introducer with the needle of the biopsy device of FIG. 1A fully inserted into the introducer.

FIG. 16 shows an exemplary alternative introducer (200), which may be used with needle (50) in place of introducer (100) described above. Introducer (200) is substantially the same as introducer (100) with certain exceptions noted below. In particular, like introducer (100), introducer (200) comprises an introducer lumen (202), a latching feature (280) and an open distal end (206). However, unlike introducer (100), introducer (200) comprises two distal leaves (204) that engage the relatively flat surfaces of needle (50).

Figure 17:
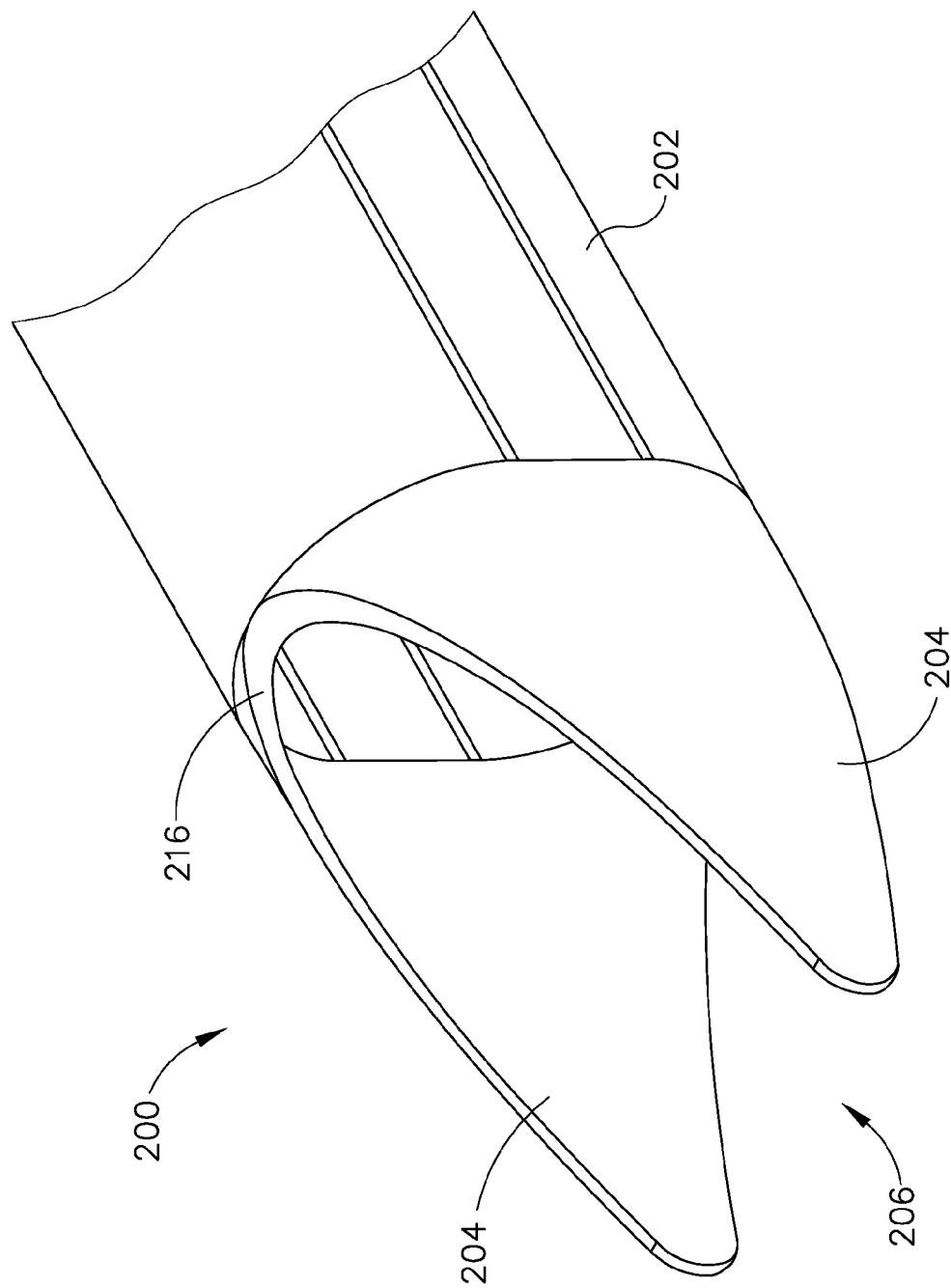
FIG. 17 depicts a perspective view of a distal end of the introducer of FIG. 16.

FIG. 17 shows a detailed perspective view of leaves (204) of introducer (200). Because introducer (200) has two leaves (204) there is no gap similar to gap (110) of introducer (100). However, leaves (204) are still symmetrical from top to bottom. Thus, introducer (200) can be inserted onto needle (50) in the orientation shown, or the opposite (upside down)

orientation. Additionally, like leaves (104), leaves (204) include a chamfered surface (216) on the top (or bottom) of each leaf (204).

Figure 18:
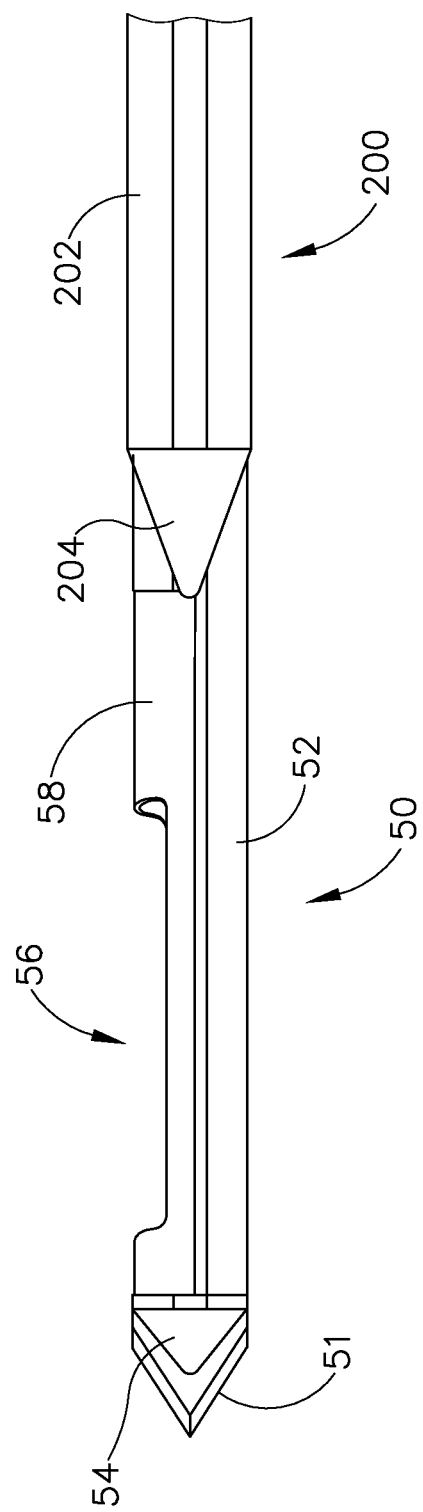
FIG. 18 depicts a side view of the needle of the biopsy device of FIG. 1A fully inserted into the introducer of FIG. 16.
Figure 19:
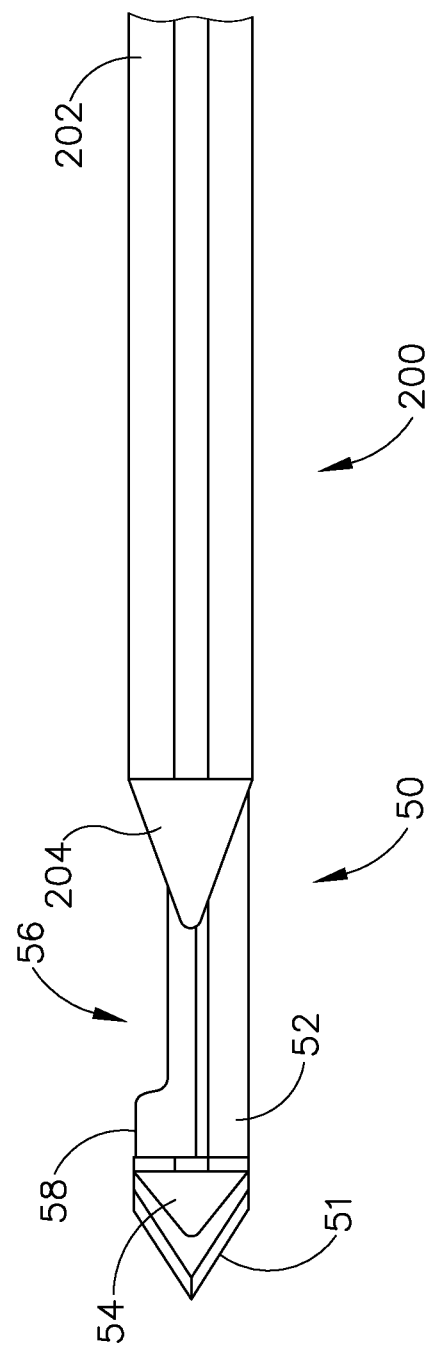
FIG. 19 depicts a side view of the needle of the biopsy device of FIG. 1A intermediately inserted into the introducer of FIG. 16.
Figure 20:
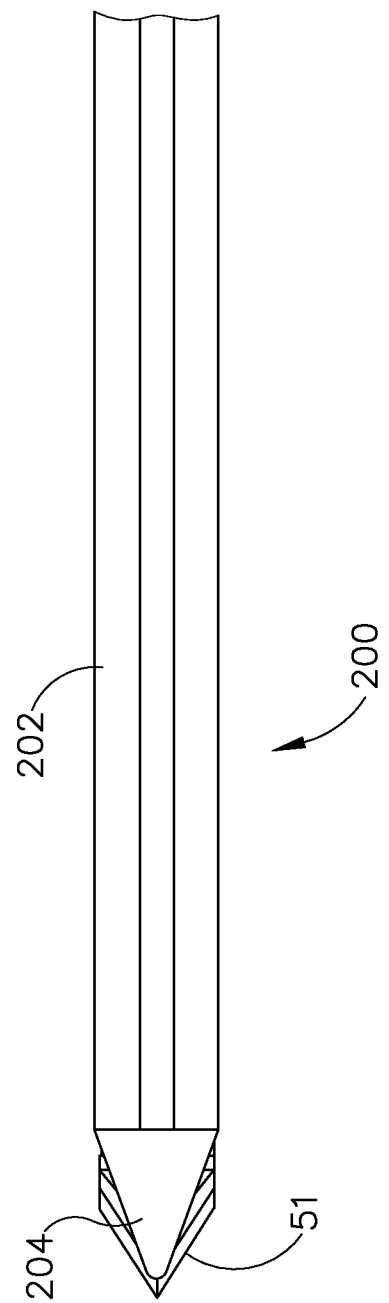
FIG. 20 depicts a side view of the needle of the biopsy device of FIG. 1A partially inserted into the introducer of FIG. 16.

FIGS. 18 through 20 show the progression of introducer (200) as needle (50) is removed (or inserted) from introducer (200). In particular, needle (50) moves from a fully inserted configuration shown in FIG. 18, to an intermediate insertion shown in FIG. 19, to a nearly removed insertion shown in FIG. 20. As can be seen, seam (55) between cannula (52) and tube (58) of needle (50) is at least partially engaged by leaves (204) of introducer (200). Although leaves (204) may directly engage the seam (55) between cannula (52) and tube (58) of needle (50), the two leaf (204) configuration provides less point of contact compared to the four leaf (104) configuration of introducer (100).

Figure 21:
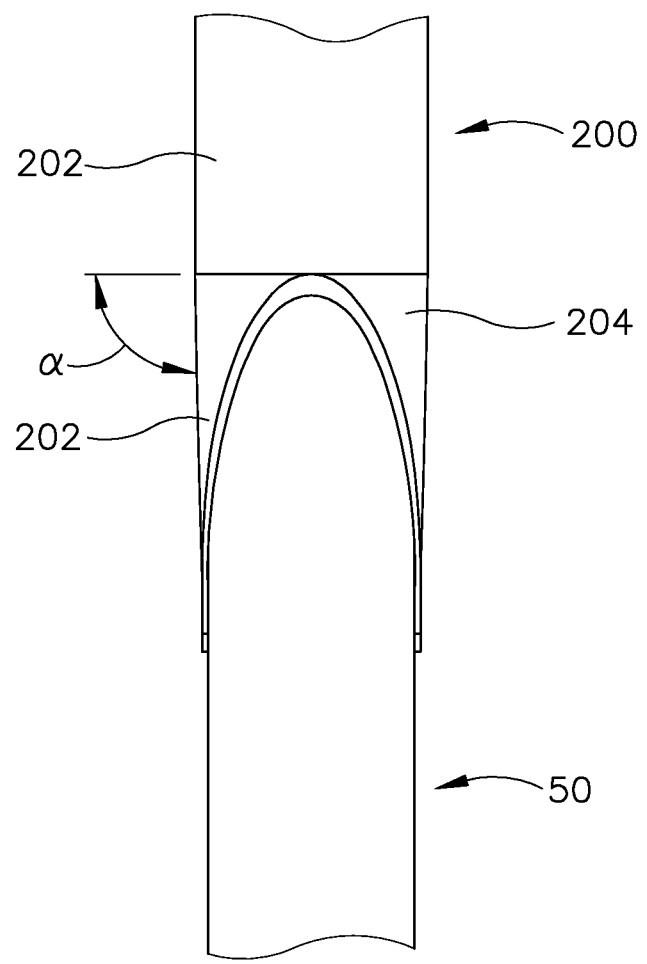
FIG. 21 depicts a top view of the needle of the biopsy device of FIG. 1A fully inserted into the introducer of FIG. 16.
Figure 22:
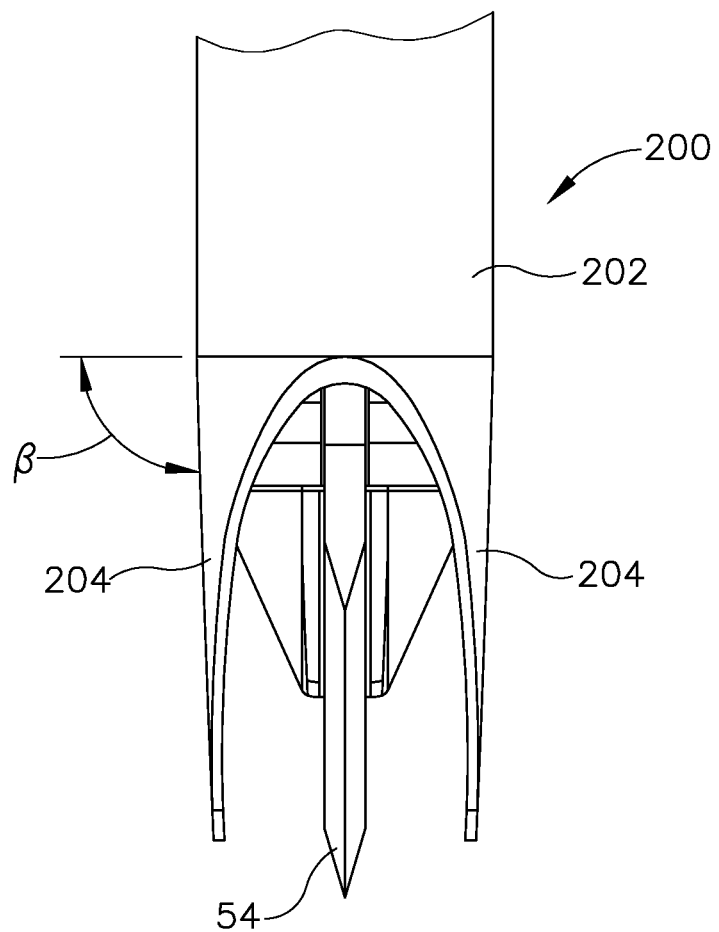
FIG. 22 depicts a top view of the needle of the biopsy device of FIG. 1A partially inserted into the introducer of FIG. 16.

FIGS. 21 and 22 show a top view of introducer (200) where leaves (204) are deflected by cannula (52) and relaxed, respectively. In the deflected state, leaves (204) are shown as having a deflected angle ($\alpha$) relative to a projection orthogonal to the longitudinal axis of introducer cannula (202). Similarly, in the relaxed state, leaves (204) are shown as having a relaxed angle ($\beta$) relative to a projection orthogonal to the longitudinal axis of introducer cannula (202). As can be seen by comparing FIGS. 21 and 22, deflected angle ($\alpha$) is smaller than relaxed angle ($\beta$). Thus, cannula (52) of needle (50) pushes leaves (204) angularly outward relative to introducer cannula (202). Although FIGS. 21 and 22 show angles ($\alpha$, $\beta$) as being substantially similar to angles ($\alpha$, $\beta$) of FIGS. 14 and 15, it should be understood that the difference between deflected angle ($\alpha$) and relaxed angle ($\beta$) may be any suitable amount that still permits deflection of leaves (204). Other leaf (204) configurations having different angles ($\alpha$, $\beta$) will be apparent to those of ordinary skill in the art in view of the teachings herein.

IV. Exemplary Use with Obturator

Figure 23:
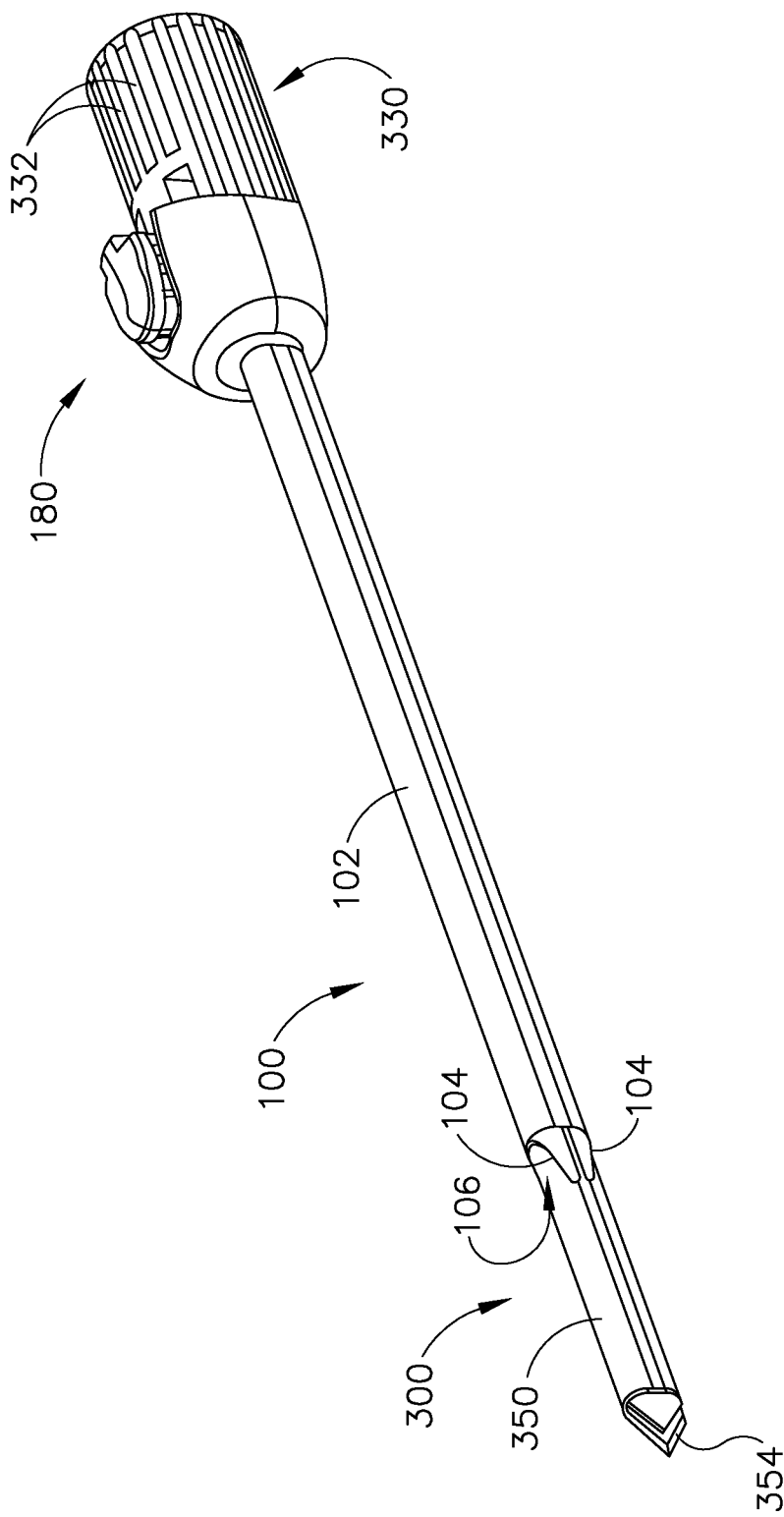
FIG. 23 depicts a perspective view of an alternative configuration of the introducer of FIG. 1A with an obturator inserted into the introducer.

FIG. 23 shows introducer (100) disposed upon an exemplary obturator (300).

Obturator (300) comprises a gripping member (330), a needle (350), and a tissue piercing tip (354). In particular, gripping member (330) may be configured with an ergonomic configuration suitable for grasping obturator (300). Gripping member (330) may also include a plurality of gripping features (332) to promote a users grip when grasping gripping member (330). Latching feature (180) of introducer (100) may be secured to gripping member (330) by a pair of slots (not shown) in gripping member (330).

Needle (350) extends distally from gripping member (330). In the present example, needle (350) has a length suitable to permit needle (350) to extend distally from the open distal end (106) of introducer (100). Needle (350) has an ovular cross-sectional shape similar to that of needle (50). Accordingly, leaves (104) of introducer (100) may engage needle (350) similar to gripping of needle (50) as described above.

Also like needle (50), the distal end of needle (350) is equipped with a sharp tissue piercing tip (354). Tissue piercing tip (354) may permit needle (350) to penetrate tissue of a patient with a relatively small penetrating force.

In a merely exemplary use of obturator (300), obturator (300) may first be inserted into introducer (100) and locked into place by latching feature (180). Obturator (300) may then be used to penetrate the tissue of a patient with needle (350) of obturator (300) and cannula (102) of introducer (100) coming into direct contact with the tissue of the patient. Gripping member (330) of obturator (300) may then be used to position obturator (300) and introducer (100) to a desired position within patient. Once obturator (300) and introducer (100) have reached a desired position, obturator (300) may be removed from introducer (100), leaving introducer (100) in place; and needle (50) of biopsy device (10) may then be inserted into introducer (100) to perform the biopsy procedure described above.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A biopsy system, comprising:
   (a) an introducer, wherein the introducer includes:
      (i) a cannula including an oval-shaped cross-section, an open distal end and an open proximal end, wherein the oval-shaped cross-section defines a lumen extending between the open distal end and the open proximal end, wherein the oval-shaped cross-section of the cannula includes at least two flat sides and two non-flat sides, and
      (ii) at least two leaves extending distally from the open distal end of the cannula, wherein at least a portion of each of the at least two leaves extends from a respective flat side of the at least two flat sides of the cannula, wherein the at least two leaves are positioned relative to the cannula to define an open space between the at least two flat sides of the cannula; and
   (b) a biopsy device, wherein the biopsy device includes:
      (i) a body, and
      (ii) an elongate needle extending distally from the body, wherein the elongate needle includes a closed distal end and an oval-shaped cross-section, wherein the closed distal end comprises a sharp tip, wherein the oval-shaped cross-section defines two straight sides;
   wherein the cannula of the introducer is configured to slidably receive the elongate needle of the biopsy device, wherein the cannula is configured to form at least two openings between the cannula and the elongate needle along the two non-flat sides when the elongate needle is slidably received within the cannula.

2. The biopsy system of claim 1, wherein the at least two leaves of the introducer consists of two leaves.

3. The biopsy system of claim 1, wherein the introducer includes four leaves.

4. The biopsy system of claim 3, wherein the four leaves are arranged in a first leaf pair and a second leaf pair, wherein each leaf pair is associated with each flat side of the oval-shaped cross-section of the cannula.

5. The biopsy system of claim 4, wherein each leaf of the first leaf pair is separated by a first gap extending between each leaf of the first leaf pair, wherein the second leaf pair is separated by a second gap extending between each leaf of the second leaf pair.

6. The biopsy system of claim 1, wherein the cannula of the introducer further includes a top portion and a bottom portion, wherein the top and bottom portions are positioned away from the at least two leaves.

7. The biopsy system of claim 6, wherein each of the top and bottom portions define a chamfered portion.

8. The biopsy system of claim 7, wherein each chamfered portion extends distally from the distal end of the cannula of the introducer.

9. The biopsy system of claim 8, wherein each chamfered portion extends transversely between the at least two leaves.

10. The biopsy system of claim 1, wherein the biopsy device and the introducer further include complementary latching features configured to selectively secure the introducer to the biopsy device.

11. The biopsy system of claim 10, wherein the complementary latching features comprise a slot and a resiliently biased latch member insertable into the slot.

12. The biopsy system of claim 1, wherein the at least two leaves extend from the open distal end of the cannula equal distances.

13. The biopsy system of claim 1, wherein at least one of the at least two leaves extends from the open distal end of the cannula further than any other leaves of the at least two leaves.

14. The biopsy system of claim 1, wherein the cannula of the introducer further includes a first longitudinal length, wherein the elongate needle of the biopsy device further includes a second length, wherein the second length is greater than the first length.

15. A biopsy system, comprising:
(a) a biopsy device, wherein the biopsy device includes:
  (i) a body,
  (ii) a needle extending distally from the body along a longitudinal axis, wherein the needle comprises a distal end and a proximal end, wherein the needle defines a lumen extending between the distal end and the proximal end, and
  (iii) a lateral aperture spaced proximally relative to the closed distal end of the needle; and
(b) an introducer, wherein the introducer includes:
  (i) a cannula defining a lumen, wherein the lumen is sized to receive the needle of the biopsy device, wherein the lumen is sized to maintain at least two gaps between the needle and the cannula when the needle is received within the lumen, and
  (ii) a first leaf set, wherein the first leaf set comprises a first pair of leaves extending distally from a first side of the distal end of the cannula, and
  (iii) a second leaf set, wherein the second leaf set comprises a second pair of leaves extending distally from a second side of the distal end of the cannula, wherein the second side of the distal end of the cannula is opposite of the first side of the distal end of the cannula.

16. A biopsy system, comprising:
(a) a biopsy device, wherein the biopsy device includes:
  (i) a body,
  (ii) a needle, wherein the needle includes a distal end and a proximal end, wherein the needle extends distally from the body at the proximal end, wherein a tip extends from the needle at the distal end, wherein the needle defines a first lumen,
  (iii) an opening spaced proximally relative to the distal end of the needle, wherein the opening is sized and configured to receive tissue samples, wherein the first lumen is in fluid communication with the opening and the body; and
(b) an introducer, wherein the introducer includes:
  (i) a cannula, wherein the cannula includes a distal end and a proximal end, wherein the cannula defines a second lumen, wherein the second lumen is sized to receive the needle of the biopsy device, wherein the second lumen is in fluid communication with the distal end of the cannula, and
  (ii) at least two pairs of leaves, wherein the at least two pair of leaves extend distally from the distal end of the cannula, wherein the at least two pair of leaves include:
    (A) a first pair extending from a first wall of the distal end of the cannula, and
    (B) a second pair extending from a second wall of the distal end of the cannula,
  wherein the first wall is positioned opposite of the second wall along the distal end of the cannula, wherein the first pair is configured to resiliently deflect inwardly toward the second pair, wherein the second pair is configured to resiliently deflect inwardly toward the first pair,
  wherein the first pair and the second pair are configured to avoid the opening of the needle when the needle is moved proximally relative to the cannula from a distal position to a proximal position, wherein the opening of the needle is configured to be positioned distally relative to the first pair and the second pair when the needle is in the distal position.

17. The biopsy system of claim 16, wherein each leaf of the at least two pair of leaves is separated by a gap extending between each leaf of the first pair and second pair.

18. The biopsy system of claim 16, wherein the first pair is associated with a first flat side of the cannula, wherein the second pair is associated with a second flat side of the cannula.

19. The biopsy system of claim 16, wherein the biopsy device and the introducer further include complementary latching features configured to selectively secure the introducer to the biopsy device.

20. The biopsy system of claim 16, wherein the distal end of the cannula includes at least two chamfered portions in between the first wall and the second wall.

* * * * *